(12) United States Patent
Paul et al.

(10) Patent No.: US 8,193,235 B2
(45) Date of Patent: Jun. 5, 2012

(54) COMPOSITIONS AND METHODS FOR ESTABLISHING AND MAINTAINING STEM CELLS IN AN UNDIFFERENTIATED STATE

(75) Inventors: Soumen Paul, Overland Park, KS (US); Debasree Dutta, Kansas City, KS (US); Soma Ray, Overland Park, KS (US); Jeffrey Aube, Lawrence, KS (US); Frank John Schoenen, Lawrence, KS (US)

(73) Assignee: University of Kansas, Kansas City, KS (US)

( * ) Notice: Subject to any disclaimer, the term of this patent is extended or adjusted under 35 U.S.C. 154(b) by 0 days.

(21) Appl. No.: 12/813,688

(22) Filed: Jun. 11, 2010

(65) Prior Publication Data

US 2010/0317100 A1   Dec. 16, 2010

Related U.S. Application Data

(60) Provisional application No. 61/249,722, filed on Oct. 8, 2009, provisional application No. 61/186,485, filed on Jun. 12, 2009.

(51) Int. Cl.
*A61K 31/164* (2006.01)
*C07D 233/64* (2006.01)

(52) U.S. Cl. ........................ 514/408; 548/400
(58) Field of Classification Search .................. 514/408; 548/400
See application file for complete search history.

(56) References Cited

U.S. PATENT DOCUMENTS

| | | | |
|---|---|---|---|
| 5,545,636 A | 8/1996 | Heath, Jr. et al. | 514/214.02 |
| 6,200,806 B1 | 3/2001 | Thomson | 435/366 |
| 2008/0171385 A1 | 7/2008 | Bergendahl et al. | 435/366 |

FOREIGN PATENT DOCUMENTS

| | | |
|---|---|---|
| EP | 0397060 | * 4/1990 |
| EP | 0397060 | * 11/1990 |
| RU | 2388759 | 5/2010 |
| WO | WO 2008/037688 A2 | 4/2008 |
| WO | WO 2008/074752 A2 | 6/2008 |
| WO | PCT/US2010/38278 | 10/2010 |

OTHER PUBLICATIONS

Gao et al. "Expression of Protein Kinase C Isoforms in Retinoic Acid-induced Differentiation of Mouse Embryonic Stem Cells into Neuron-like Cells" Chinese Medical Journal 2007 vol. 120(18):1639-1642.
Amit et al. "Clonally Derived Human Embryonic Stem Cell Lines Maintain Pluripotency and Proliferative Potential for Prolonged Periods of Culture" Developmental Biology 2000 227:271-278.
Dutta et al. "Activation of the VEGFR1 Chromatin Domain" The Journal of Biological Chemistry 2008 283(37):25404-25413.
Evans, M. J. and Kaufmann, M. H. "Establishment in Culture of Pluripotential Cells from Mouse Embryos" Nature 1981 292(5818):154-156.
Heo, J. S. and Han, H. J. "ATP Stimulates Mouse Embryonic Stem Cell Proliferation via Protein Kinase C, Phosphatidylinositol 3-Kinase/Akt, and Mitogen-Activated Protein Kinase Signaling Pathways" Stem Cells 2006 24:2637-2648.
Niwa et al. "Self-Renewal of Pluripotent Embryonic Stem Cells Is Mediated via Activation of STAT3" Genes and Development 1998 12:2048-2060.
Odorico et al. "Multilineage Differentiation from Human Embryonic Stem Cell Lines" Stem Cells 2001 19:193-204.
Prudhomme et al. "Multivariate Proteomic Analysis of Murine Embryonic Stem Cell Self-Renewal Versus Differentiation Signaling" PNAS 2004 101(9):2900-2905.
Sato et al. "Maintenance of Pluripotency in Human and Mouse Embryonic Stem Cells through Activation of Wnt Signaling by a Pharmacological GSK-3-Specific Inhibitor" Nature Medicine 2004 10(1):55-63.
Smith et al. "Inhibition of Pluripotential Embryonic Stem Cell Differentiation by Purified Polypeptides" Nature 1988 336(6200):688-690.
Takahashi, K. and Yamanaka, S. "Induction of Pluripotent Stem Cells from Mouse Embryonic and Adult Fibroblast Cultures by Defined Factors" Cell 2006 126:663-676.
Wang et al. "Direct Binding to Ceramide Activates Protein Kinase C$\zeta$ before the Formation of a Pro-Apoptotic Complex with PAR-4 in Differentiating Stem Cells" The Journal of Biological Chemistry 2005 280(28):26415-26424
Williams et al. "Myeloid Leukaemia Inhibitory Factor Maintains the Developmental Potential of Embryonic Stem Cells" Nature 1988 336(6200):684-687.
Ying et al. "BMP Induction of Id Proteins Suppresses Differentiation and Sustains Embryonic Stem Cell Self-Renewal in Collaboration with STAT3" Cell 2003 115:281-292.
Ying et al. "The Ground State of Embryonic Stem Cell Self-Renewal" Nature 2008 453:519-523.
Zhou et al. "Differentiation of Nonbeating Embryonic Stem Cells into Beating Cardiomyocytes Is Dependent on Downregulation of PKC$\beta$ and $\zeta$ in Concert with Upregulation of PKC$\epsilon$" Developmental Biology 2003 255:407-422.
Hwang et al. "Chemicals that Modulate Stem Cell Differentiation" PNAS 2008 vol. 105(21):7467-7471.
Gao et al. "Expression, of Protein Kinase C Isoforms in Retinoic Acid-induced Differentiation of Mouse Embryonic Stem Cells into Neuron-like Cells" Chinese Medical Journal 2007 vol. 120(18):1639-1642.
Gong et al. "Discovery of Potent and Bioavailable GSK-3$\beta$ Inhibitors" Bioorganic & Medicinal Chemistry Letters 2010 vol. 20:1693-1696.

* cited by examiner

*Primary Examiner* — Susannah Chung
(74) *Attorney, Agent, or Firm* — Licata & Tyrrell P.C.

(57) ABSTRACT

The present invention embraces compositions and methods for establishing and maintaining stem cells and inhibiting stem cell differentiation using a selective Protein Kinase C (PKC) inhibitor.

1 Claim, 7 Drawing Sheets

```
                       SEQUENCE LISTING

<160> NUMBER OF SEQ ID NOS: 66

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
ctcaccctgg gcgttctct                                                  19
```

```
<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 2
aggcctcgaa gcgacaga                                                    18

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
tgctactgag atgctctgca ca                                               22

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
tgccttgaag aggcaggtct                                                  20

<210> SEQ ID NO 5
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 5
gcacatgaac ggctggagca acg                                              23

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
tgctgcgagt aggacatgct gtagg                                            25

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 7
ccctggaaga caccccaat                                                   19

<210> SEQ ID NO 8
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 8
```
tggacatggc cccacaat                                                                   18

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
agatgaatgg cctcagcagg                                                                 20

<210> SEQ ID NO 10
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 10
caagccgccg tgatgaa                                                                    17

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
ctgcaggcca ctgaaaagtt                                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
aggtgtctgc aagcgagagt                                                                 20

<210> SEQ ID NO 13
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 13
ccaacctatg cggacaattc atctgc                                                          26

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 14
gtgtaatgtg caggggagcc tcgaa                                                           25

<210> SEQ ID NO 15
<211> LENGTH: 23
<212> TYPE: DNA
<213> ORGANISM: Artificial Sequence

```
<220> FEATURE:
<223> OTHER INFORMATION: Synthetic oligonucleotide

<400> SEQUENCE: 15
ggactggagc atgtatccta gct                                              23

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
taaccaccgt agtccgggta ct                                               22

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
ggcagtttct tcttgggatt t                                                21

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
gcgatcctgc tttcttctgt                                                  20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
aacaccaact ccatcagttc                                                  20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
atctggataa tgggtcctct                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gaagccctgg agaacctctt                                                  20
```

-continued

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
tcgactgtct gtgcaagtcc                                               20

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 23
tccaacaagg aaccctgctt c                                             21

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
ttgccgacta tgccagtcaa g                                             21

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
tcatcagcct gacagagacc                                               20

<210> SEQ ID NO 26
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 26
aggtgcagga cgcacactc                                                19

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 27
aggaggccga ggaatggt                                                 18

<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 28
catcgttgtt ccggttgg                                                 18

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
cccctggaca tctctactcc                                               20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
gggttcacac accagcactc                                               20

<210> SEQ ID NO 31
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 31
ctgaacggcg agatcagtg                                                19

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 32
ctcctgaagg gctggagtc                                                19

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ggacatcagc atcctgtcct                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
ctcctggtga aatggctgat                                               20

<210> SEQ ID NO 35
<211> LENGTH: 18
<212> TYPE: DNA
<213> ORGANISM: Artificial Sequence

```
<220> FEATURE:
<223> OTHER INFORMATION: Synthetic oligonucleotide

<400> SEQUENCE: 35
caggtggtcc tggcagag                                                    18

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
gagagagggt cccagagtcc                                                  20

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 37
tgcccccatg tttgtgatg                                                   19

<210> SEQ ID NO 38
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 38
tgtggtcatg agcccttcc                                                   19

<210> SEQ ID NO 39
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 39
ttgggaccag ctagagcaat                                                  20

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
ccaggcttgt ctaccaccat                                                  20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
tgggctgaaa tactgggttc                                                  20
```

```
<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
ttgaatgttc gtgtgccaat                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
cctaggaaaa ggctgggaac                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
gtggtgtgcc attgtttctg                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
ccttcccata caccacaacc                                               20

<210> SEQ ID NO 46
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 46
cccctccttc caaattaagc                                               20

<210> SEQ ID NO 47
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 47
cgtccgcctt cgtacaagtt gtct                                          24

<210> SEQ ID NO 48
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 48
```

-continued gtgttaggag ctagggagag tcagggtag                                29

<210> SEQ ID NO 49
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 49
gcgattgtct cacttctttc tccacac                                  27

<210> SEQ ID NO 50
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 50
aggctggcgt ccgagtccat                                          20

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
atttggaaac aaacgcccta                                          20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
agggaacaca ccaactttcg                                          20

<210> SEQ ID NO 53
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 53
ccactcactc tgaggctcgc tgtag                                    25

<210> SEQ ID NO 54
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 54
ccaaagcaga cctgaggctc gaa                                      23

<210> SEQ ID NO 55
<211> LENGTH: 19
<212> TYPE: DNA
<213> ORGANISM: Artificial Sequence

```
<220> FEATURE:
<223> OTHER INFORMATION: Synthetic oligonucleotide

<400> SEQUENCE: 55
atcccggtaa gttctgttg                                              19

<210> SEQ ID NO 56
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 56
ggacctctgt gaggaagtg                                              19

<210> SEQ ID NO 57
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 57
gttgttttgt tttggttttg gatat                                       25

<210> SEQ ID NO 58
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 58
atgggttgaa atattgggtt tattta                                      26

<210> SEQ ID NO 59
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 59
ccaccctcta accttaacct ctaac                                       25

<210> SEQ ID NO 60
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 60
gaggatgttt tttaagtttt tttt                                        24

<210> SEQ ID NO 61
<211> LENGTH: 25
<212> TYPE: DNA
<213> ORGANISM: Artificial Sequence
```

```
<220> FEATURE:
<223> OTHER INFORMATION: Synthetic oligonucleotide

<400> SEQUENCE: 61
aatgtttatg gtggattttg taggt                                              25

<210> SEQ ID NO 62
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 62
cccacactca tatcaatata ataac                                              25

<210> SEQ ID NO 63
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 63
ggttttagaa ataattggta tacga                                              25

<210> SEQ ID NO 64
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 64
ctattaacac tacaccctct cgac                                               24

<210> SEQ ID NO 65
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 65
atttgtgagt ataaggattg atcgg                                              25

<210> SEQ ID NO 66
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 66 tttcttttaaa ataaaatttc acgta                                             25
```

US 8,193,235 B2

COMPOSITIONS AND METHODS FOR ESTABLISHING AND MAINTAINING STEM CELLS IN AN UNDIFFERENTIATED STATE

INTRODUCTION

This application claims benefit of priority to U.S. Provisional Application Ser. No. 61/249,722, filed Oct. 8, 2009, and 61/186,485, filed Jun. 12, 2009, the contents of which are incorporated herein by reference in their entireties.

BACKGROUND OF THE INVENTION

Embryonic stem cells, referred to as ES cells, are derived from the inner cell mass (ICM) of embryos in the blastocyst phase, and can be cultured and maintained in vitro while being kept in an undifferentiated state. ES cells are pluripotent, possessing the capability of developing into any organ or tissue type or, at least potentially, into a complete embryo. For example, ES cells can differentiate and give rise to a succession of mature differentiated cells. Differentiation has been shown in tissue culture and in vivo.

An important application of human ES cells is their use in regenerative medicine, tissue engineering, and cell therapy: the treatment of symptoms, diseases, conditions, and disabilities with ES cell-derived replacement cells and tissues. Many diseases and disorders result from disruption of cellular function or destruction of tissues of the body. A wide spectrum of diseases may be treated based upon both the possession of a population of cells having multi-lineage potential and an understanding of the mechanisms that regulate embryonic cell development. Pluripotent stem cells that are stimulated in vitro to develop into specialized cells offer the possibility of a renewable source of replacement cells and tissue to treat numerous diseases, conditions, and disabilities.

ES cells have been derived from mouse (Evans & Kaufman (1981) *Nature* 292:154-156; Martin (1981) *Proc. Natl. Acad. Sci. USA* 78:7634-7639), hamster (Doetschmann, et al. (1999) *Dev. Biol.* 127:224-227), sheep (Handyside, et al. (1987) *Roux's Arch. Dev. Biol.* 198:48-55; Notarianni, et al. (1991) *J. Reprod. Fertil.* 43:255-260), cow (Evans, et al. (1990) *Theriogenology* 33:125-128), rabbit (Giles, et al. (1993) *Mol. Reprod. Dev.* 36:130-138), mink (Sukoyan, et al. (1993) *Mol. Reprod. Dev.* 36:148-158) and pig (Piedrahita, et al. (1988) *Theriogenology* 29:286; Evans, et al. (1990) supra; Notarianni, et al. (1990) *J. Reprod. Fertil. Suppl.* 41:51-56). The derivation of human ES cells has also been reported (Thomson, et al. (1998) *Science* 282:1145-1147; Shamblott, et al. (1998) *Proc. Natl. Acad. Sci. USA* 95:13726-13731).

Various methods have been described for maintaining ES cell pluripotency and to derive new ES and induced pluripotent stem (iPS) cells (Evans & Kaufman (1981) *Nature* 292: 154-156; Niwa, et al. (1998) *Genes Dev.* 12:2048-2060; Sato, et al. (2004) *Nature Med.* 10:55-63; Takahashi & Yamanaka (2006) *Cell* 126:663-676; Ying, et al. (2003) *Cell* 115:281-292; Ying, et al. (2008) *Nature* 453:519-523). For example, screens for molecules that increase cloning efficiency have been described (U.S. Patent Application No. 2008/0171385). In addition, it has been shown that mouse ES cells can remain undifferentiated indefinitely in the presence of an embryonic fibroblast feeder layer. Similarly, it is reported that a feeder layer composed of mitotically inactivated mouse embryonic fibroblasts (MEFs) or other fibroblasts is required for human ES cells to remain in an undifferentiated state (see, e.g., U.S. Pat. No. 6,200,806; Amit, et al. (2000) Dev. Biol. 227:271-78; Odorico, et al. (2001) Stem Cells 19:193-204). However, while mouse ES cells will also remain undifferentiated in the absence of an embryonic fibroblast feeder layer so long as the medium is supplemented with leukemia inhibitory factor (LIF) (Smith, et al. (1988) Nature 336:688-690; Williams, et al. (1988) Nature 336:684-687), human ES cells differentiate or die in the absence of a fibroblast feeder layer, even when the medium is supplemented with LIF (Thomson, et al. (1998) supra).

SUMMARY OF THE INVENTION

The present invention features methods for establishing and maintaining stem cells and for inhibiting stem cell differentiation using a selective Protein Kinase C (PKC) inhibitor. According to particular embodiments of the invention, the PKC inhibitor inhibits at least the zeta isoform of PKC. In other embodiments, the PKC inhibitor further inhibits the alpha and delta isoforms of PKC. In specific embodiments, the inhibitor is used in the range of 100 nm to 5 µM. In particular embodiments, the PKC inhibitor has a structure as set forth in Formulae I-IV as described herein. Stem cell lines which can be established and maintained in accordance with the methods of the invention include those isolated from mouse, rat or human. In particular embodiments, the stem cells are embryonic stem cells, adult stem cells, induced pluripotent stem cells, or cancer stem cells.

DETAILED DESCRIPTION OF THE INVENTION

Figure 1A:
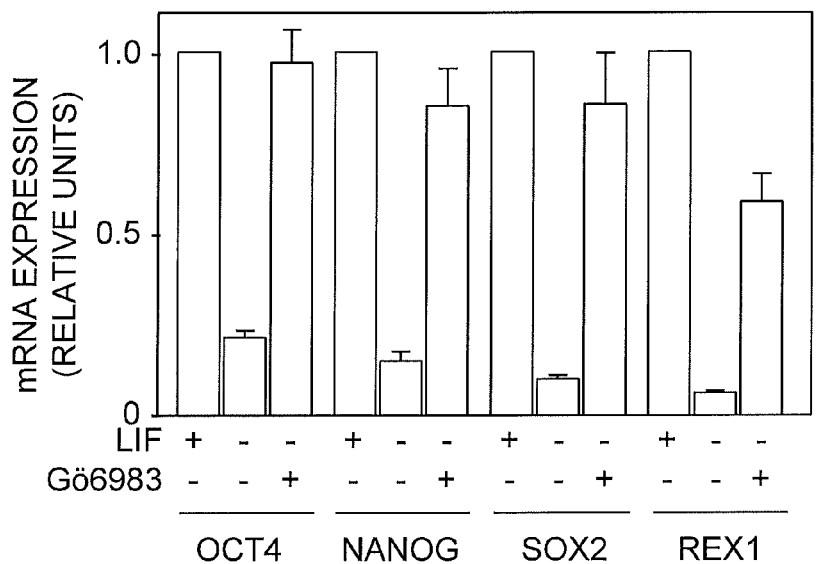
FIG. 1 shows that Gö6983 treated ES cells maintain the expression of pluripotency markers (FIG. 1A) without induction of differentiation markers (FIG. 1B), even in the absence of serum, LIF, and BMP4 (FIG. 1C) and in the presence of collagen IV (FIG. 1D). The plots show quantitative RT-PCR analysis of markers (mean±standard error). Data presented in FIG. 1D is RT-PCR analysis of lineage-specific marker expression in E14 cells upon withdrawal of Gö6983 after five passages on collagen IV.
FIG. 1E, Differentiation potential of collagen IV was determined by measuring mRNA expression of pluripotency and lineage markers. mRNA levels were measured after culturing on collagen IV for 5 days in the absence and presence of Gö6983 (mean±standard error; three independent experiments).

Highly orchestrated signaling mechanisms and gene expression patterns endow embryonic stem (ES) cells with the capacity to maintain pluripotency or to differentiate into other cell types of an organism. It has now been found that pharmacological inhibition of Protein Kinase C (PKC) isoforms by a selective PKC inhibitor maintains the undifferentiated phenotype of multiple ES cell lines in the absence of leukemia inhibitory factor (LIF) and mouse embryonic fibroblast (MEF) feeder cells. Inhibition of PKC function also strongly inhibits differentiation of stem cells under strong differentiation cues like culturing on Collagen IV or treatment with retinoic acid (RA), which strongly induce mesodermal and ectodermal differentiation, respectively (Nishikawa, et al. (1998) *Development* 125:1747; Lee, et al. (2007) *Stem Cells* 25:2191). Stem cells maintained for multiple passages with PKC inhibitor generate chimeric mice when injected into blastocyst. In addition, new stem cell lines can be efficiently derived, and propagated in the presence of the PKC inhibitor. Inhibition of stem cell differentiation is functionally reversible as withdrawal of the inhibitor leads to a multidifferentiation program in stem cells, i.e., the cells can be induced to differentiate into one more lineages. Mechanistic analysis revealed that PKC inhibition of ES cell differentiation is associated with the continuous presence of polycomb repressor complex 2 (PRC2) at the developmental genes. These results indicate that PKC signaling is an important pathway to dictate maintenance of stem-ness vs. differentiation of mammalian embryonic stem cells and also indicate that the use of PKC inhibitors like Gö6983 are useful for establishing new mammalian stem cells for regenerative medicine purposes.

Accordingly, the present invention embraces methods for establishing and maintaining stem cells in an undifferentiated state by exposing the cells to a selective Protein Kinase C inhibitor. As is conventional in the art, a "stem cell" is a cell characterized by the ability to renew itself through mitotic cell division and differentiate into a diverse range of specialized cell types. In this respect, a stem cell of the invention possesses pluripotency and self-renewal. As used herein, the term "pluripotent" or "pluripotency" refers to the ability of a cell to develop into one of ectodermal, endodermal and mesodermal cell fate or lineage. Stem cells embraced by the present invention include, but are not limited to embryonic stem cells, adult stem cells, induced pluripotent stem cells, and cancer stem cells. "Embryonic stem cell" include cells obtained from embryos or fetuses. Adult stem cells tissue-specific stem cells such as hematopoietic stem cells. In adult organisms, tissue-specific stem cells and progenitor cells replenish specialized cells, and also maintain the normal turnover of regenerative organs, such as blood, skin, or intestinal tissues. Induced pluripotent stem cells are a type of pluripotent stem cell artificially derived from a non-pluripotent cell, typically an adult somatic cell, by inducing "forced" expression of certain genes (Takahashi & Yamanaka (2006) *Cell* 126:663). Cancer stem cells are cancer cells (i.e., found within tumors or hematological cancers) that possess characteristics associated with normal stem cells, specifically the ability to give rise to all cell types found in a particular cancer sample. The term "cell" as used herein refers to individual cells, cell lines, or cultures derived from such cells. A "cell line" refers to a composition comprising isolated cells of the same type.

In accordance with the present invention, a pluripotent stem cell line is established by culturing cells, such as embryonic cells or adult cells, with a selective Protein Kinase C inhibitor. Embryonic cells, such as blastocytes or cells isolated from a blastocyst (e.g., fibroblasts) can be isolated from any mammal including, but not limited to, mice, rats, pigs, humans and the like. The establishment of iPSCs is also embraced by this method, wherein the cells being contacted with the PKC inhibitor are adult cells that express one or more reprogramming factors (e.g., Oct4, Sox2, Klf4 and/or c-Myc). As described herein, the cells can be plated directly on gelatin-coated plates containing the PKC inhibitor to establish a pluripotent stem cell line. By "isolated" herein is meant free from at least some of the constituents with which a component, such as a cell, is found in its natural state. More specifically, isolated can mean free from 70%, 80%, 90%, or 95% of the constituents with which a component is found in its natural state.

When passaged or cultured in the presence of a PKC inhibitor, stem cells maintain their undifferentiated phenotype or pluripotency. As such, the present invention also embraces a method for maintaining the undifferentiated phenotype of a stem cell by culturing or contacting an isolated stem cell with a selective Protein Kinase C inhibitor. The terms "maintaining" and "maintenance" refer to the stable preservation of the characteristics or phenotypes of the stem cells when cultured under specific culture conditions. Such phenotypes can include the cell morphology and gene expression profiles of the stem cells, which can be determined using the techniques described herein. For example, stem cells maintained or established in accordance with the present invention express pluripotency markers including Oct4, Nanog, Sox2 and Rex-1. The term "maintain" can also encompass the propagation of stem cells, or an increase in the number of stem cells being cultured. The invention contemplates culture conditions that permit the stem cells to remain pluripotent, while the stem cells may or may not continue to divide and increase in number.

As used herein, the terms "develop", "differentiate" and "mature" all refer to the progression of a cell from the stage of having the potential to differentiate into at least two different cellular lineages to becoming a specialized and terminally differentiated cell. As such, the term "undifferentiated" is intended to mean a cell that has not progressed to a specialized and terminally differentiated stage.

According to particular embodiments of the invention, the undifferentiated phenotype of the embryonic stem cells is maintained in the absence of a feeder cell or leukemia inhibitory factor (LIF). The term "feeder cell" refers to a culture of cells that grows in vitro and secretes at least one factor into the culture medium, and that can be used to support the growth of another cell of interest in culture.

As demonstrated herein, culturing of stem cells in the presence of a selective PKC inhibitor inhibits differentiation of the stem cell, even under differentiation conditions, e.g., absence of LIF or presence of differentiation factors such as collagen IV. Accordingly, the present invention also embraces a method of inhibiting differentiation of a stem cell by contacting the stem cell with a selective PKC inhibitor. For the purposes of the present invention, differentiation can be inhibited partially or completely depending on the PKC inhibitor selected. Partial inhibition is intended to mean that 20%, 30%, 40%, 50%, 60%, 70% or 80% of the cells in the culture exhibit a differentiated phenotype, whereas complete inhibition is intended to mean that 95%, 99%, or 100% of the cells in the culture are undifferentiated.

The selection of the selective PKC inhibitor to be used in accordance with the present invention will be dependent upon the effect to be achieved, i.e., partial or complete inhibition of differentiation or partial or complete maintenance of the undifferentiated phenotype. For example, inhibition of PKC zeta alone can provide partial inhibition of differentiation, whereas a combination of inhibitors, or an inhibitor that inhibits multiple PKC isoforms, can provide complete inhibition of differentiation. Thus, the methods of this invention can employ any PKC inhibitor known in the art including non-specific PKC inhibitors and specific PKC inhibitors of different isoforms. However, in particular embodiments, the inhibitor of the invention is selective in that it inhibits the activity of one or more PKC isoforms and does not inhibit other protein kinases, e.g., protein kinase A, casein kinase I, protein kinase G or rho-associated kinase II. Information about selective PKC inhibitors, and methods for their preparation are readily available in the art. For example, various PKC inhibitors and their preparation are described in U.S. Pat. Nos. 5,621,101; 5,621,098; 5,616,577; 5,578,590; 5,545,636; 5,491,242; 5,488,167; 5,481,003; 5,461,146; 5,270,310; 5,216,014; 5,204,370; 5,141,957; 4,990,519; and 4,937,232, all of which are incorporated herein by reference. Commercial sources of selective protein kinase C inhibitors include Calbiochem, Sigma, and Tocris Biosciences. By way of illustration, Table 1 lists PKC inhibitors with selectivity for one or more PKC isoforms.

TABLE 1

| Inhibitor | Isoform Specificity* | | | | | |
|---|---|---|---|---|---|---|
|  | α | β | γ | δ | ζ | ε |
| Chelerythrine chloride C | X | X | X | X | X |  |
| Gö6983 | X | X | X | X | X |  |
| Gö6976 | X | X[2] |  |  |  |  |
| Ro-31-8425 | X | X[1, 2] | X |  |  | X |
| Rottlerin |  |  |  | X |  |  |
| Bisindolylmaleimide I | X | X[1] |  | X | X | X |
| ISSI-3521 | X |  |  |  |  |  |
| Midostaurin | X | X[1, 2] | X |  |  |  |
| Calphostin C | X | X[1, 2] | X | X |  | X |
| Ro-31-8220 | X | X[1, 2] | X |  |  |  |

*Isoforms not listed may also be inhibited.
[1]PKC β1.
[2]PKC β2.

Preferably, the present invention employs those Protein Kinase C inhibitors that effectively inhibit at least the ζ isozyme. In certain embodiments, one or more PKC inhibitors are employed wherein said inhibitors effectively inhibit at least the ζ, α and δ isoforms. In particular embodiments, one or more PKC inhibitors are employed wherein said inhibitors effectively inhibit at least the α, β, γ, δ and ζ isoforms of PKC. In certain embodiments, the inhibitor employed in the instant methods is a bisindolylmaleimide. In so far as 2-(6-Phenyl-1H-indazol-3-yl)-1H-benzo[d]imidazoles have also been shown to be potent and isoform selective PKC ζ inhibitors (Trujillo, et al. (2009) *Bioorg. Med. Chem. Lett.* 19:908-911), the present invention also embraces the use of benzoimidazoles in the instant methods.

Examples of bisindolylmaleimides include Gö6983 (3-[1-[3-(dimethylamino)propyl]5-methoxy-1H-indol-3-yl]-4-(1H-indol-3-yl)-1H-pyrrole-2,5-dione) and bisindolylmaleimide I (GF109203X).

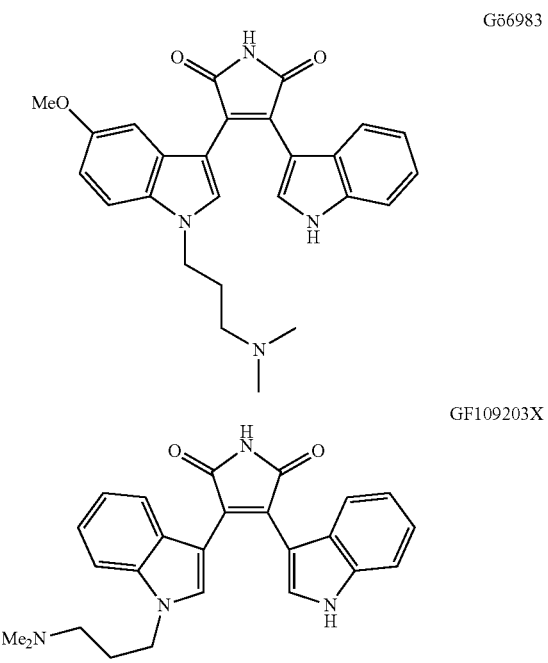

Gö6983

GF109203X

Moreover, PKC inhibitors can be derived from the structure of bisindolylmaleimides and/or benzoimidazoles. PKC inhibitors particularly embraced by the invention are as set forth in formulae I, II, III, IV, and V,

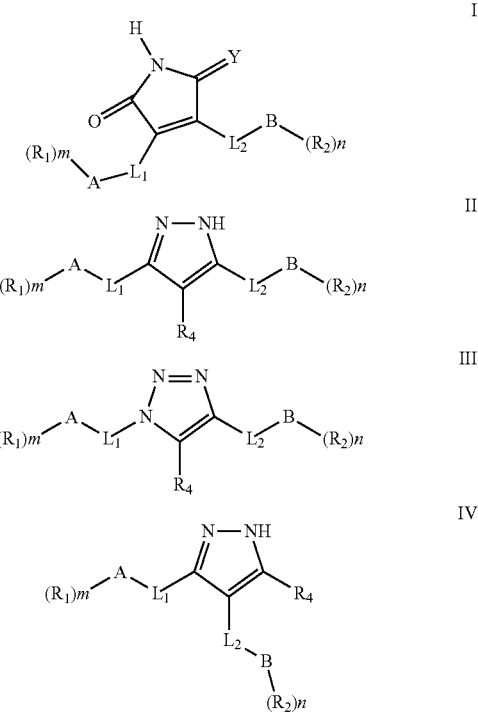

I

II

III

IV

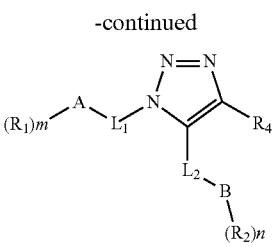

V or a pharmaceutically acceptable salt, hydrate, or prodrug thereof.

In any of formula I, II, III, IV, or V, each of $R_1$ and $R_2$ is independently selected from —H, halogen, haloalkoxy, —CN, —$NO_2$, —$OR_3$, —$N(R_3)R_3$, —$S(O)O$-$2R_3$, —$N(R_3)C(=O)N(R_3)R_3$, —$N(R_3)C(=O)N(R_3)R_3$, —$SO_2N(R_3)R_3$), —$CO_2R_3$, —$C(=O)N(R_3)R_3$, —$C(=NR_5)N(R_3)R_3$, —$C(=NR_5)NR_3$, —$N(R_3)SO_2R_3$, —$N(R_3)C(O)R_3$, —$NCO_2R_3$, —$N(R_3)C(O)2R_3$ (—$N(R_3)C(O)2R_3$), —$C(=O)R_3$, optionally substituted alkoxy, optionally substituted lower alkyl, optionally substituted aryl, optionally substituted lower arylalkyl, optionally substituted cycloalkyl, optionally substituted cycloalkylalkyl, optionally substituted heteroaryl, optionally substituted heteroarylalkyl, optionally substituted heterocyclyl, or optionally substituted lower heterocyclylalkyl;

Y is selected from O, or HH;

each of m and n is independently 1 to 5;

each of A and B is independently selected from a five- to ten-membered aryl of heteroaryl;

$R_3$ is selected from —H, optionally substituted lower alkyl, optionally substituted aryl, optionally substituted lower arylalkyl, optionally substituted heterocyclyl, or optionally substituted lower heterocyclylalkyl;

two of $R_3$, together with nitrogen to which they are attached, can combine to form an optionally substituted heterocycyl containing between one and three additional heteroatoms;

$R_4$ is selected from —H and optionally substituted lower alkyl;

each $R_5$ is independently selected from —H, —CN, —$NO_2$, —$OR_3$, —$S(O)O$-$2R_3$, —$CO_2R_3$, optionally substituted lower alkyl, optionally substituted lower alkenyl, or optionally substituted lower alkynyl; and each of $L_1$ and $L_2$ is independently selected from absent and —$C(R_3)(R_3)$—, —$C(R_3)(R_3)C(R_3)(R_3)$—, —$C(R_3)(R_3)C(R_3)(R_3)C(R_3)(R_3)$—, —$C(R_3)(R_3)C(R_3)(R_3)C(R_3)(R_3)C(R_3)(R_3)$—.

Examples of "halogen" groups include fluorine, chlorine, bromine and iodine.

"Haloalkoxy" means a group of the formula —OR, wherein R is a haloalkyl group. Examples of haloalkoxy moieties include, but are not limited to, trifluoromethoxy, difluoromethoxy, 2,2,2-trifluoroethoxy, and the like.

"Alkoxy" means a moiety of the formula —OR, wherein R is an alkyl moiety. Examples of alkoxy groups include, but are not limited to, methoxy, ethoxy, isopropoxy, tert-butoxy and the like.

"Lower alkyl" refers to a linear or branched alkyl group of one to six carbon atoms, i.e., $C_1$-$C_6$ alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Lower alkenyl" refers to an alkenyl group containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

"Lower alkynyl" refers to an alkynyl group containing from two to eight carbon atoms in the principal chain and up to 20 carbon atoms. They may be straight or branched chain and include ethynyl, propynyl, butynyl, isobutynyl, hexynyl, and the like.

The term "aryl" means an aromatic radical having 4 to 18 carbon atoms and includes heteroaromatic radicals. Examples include monocyclic groups, as well as fused groups such as bicyclic groups and tricyclic groups. Some examples include phenyl group, indenyl group, 1-naphthyl group, 2-naphthyl group, azulenyl group, heptalenyl group, biphenyl group, indacenyl group, acenaphthyl group, fluorenyl group, phenalenyl group, phenanthrenyl group, anthracenyl group, cyclopentacyclooctenyl group, and benzocyclooctenyl group, pyridyl group, pyrrolyl group, pyridazinyl group, pyrimidinyl group, pyrazinyl group, triazolyl group, tetrazolyl group, benzotriazolyl group, pyrazolyl group, imidazolyl group, benzimidazolyl group, indolyl group, isoindolyl group, indolizinyl group, purinyl group, indazolyl group, furyl group, pyranyl group, benzofuryl group, isobenzofuryl group, thienyl group, thiazolyl group, isothiazolyl group, benzothiazolyl group, oxazolyl group, and isoxazolyl group.

"Lower arylalkyl" refers to an arylalkyl where the "alkyl" portion of the group has one to six carbons; this can also be referred to as $C_{1-6}$ arylalkyl.

A "cycloalkyl" group refers to a group with three to ten carbons, and it may, for example, be a monocyclic group such as cyclopropyl, cyclobutyl, cyclopentyl, cyclohexyl or cyclooctyl, or a condensed polycyclic group. Further, the secondary substituent in these substitutable groups may, for example, be halogen, alkyl, alkoxy or hydroxy.

"Cycloalkylalkyl" means a group of the formula —R'—R", where R' is alkylene (e.g., a linear saturated divalent hydrocarbon radical of one to six carbon atoms or a branched saturated divalent hydrocarbon radical of three to six carbon atoms), and R" is cycloalkyl as defined herein.

"Heteroaryl" means a monocyclic, bicyclic or tricyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, pyridazinyl, thiophenyl, furanyl, pyranyl, pyridinyl, pyrrolyl, pyrazolyl, pyrimidyl, quinolinyl, isoquinolinyl, quinazolinyl, benzofuranyl, benzothiophenyl, benzothiopyranyl, benzimidazolyl, benzoxazolyl, benzooxadiazolyl, benzothiazolyl, benzothiadiazolyl, benzopyranyl, indolyl, isoindolyl, indazolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like.

"Heteroarylalkyl" refers to a radical-$R_aR_b$ where $R_a$ is an alkylene group and $R_b$ is a heteroaryl group as described herein.

"Heterocyclyl" means a monovalent saturated moiety composed of one to three rings, incorporating one, two, three, or four heteroatoms (chosen from nitrogen, oxygen or sulfur). The heterocyclyl ring may also be optionally substituted. Examples of heterocyclyl moieties include, but are not limited to, optionally substituted piperidinyl, piperazinyl, homopiperazinyl, azepanyl, pyrrolidinyl, pyrazolidinyl, imidazolinyl, imidazolidinyl, oxazolidinyl, isoxazolidinyl, morpholinyl, thiazolidinyl, isothiazolidinyl, thiadiazolylidinyl, benzothiazolidinyl, benzoazolylidinyl, dihydrofuranyl, tetrahydrofuryl, dihydropyranyl, tetrahydropyranyl, thiamorpholinyl, thiamorpholinylsulfoxide, thiamorpholinylsulfone, dihydroquinolinyl, dihydrisoquinolinyl, tetrahydroquinolinyl, tetrahydrisoquinolinyl, and the like. Preferred heterocyclyl include tetrahydropyranyl, tetrahydrofuranyl, piperidinyl, piperazinyl and pyrrolidinyl.

The term "lower heterocyclylalkyl" refers to lower alkyl groups as defined herein wherein at least one of the hydrogen atoms of the lower alkyl group is replaced by a heterocyclyl group as described herein.

The term "optionally substituted" means, in reference to the optionally substituted group, the group may have one or more substituents including hydroxy, alkyl, alkoxy, thiol, alkylthio, arylthio, aralkylthio, halogen, amino, carboxylic acid, and carboxylate alkyl ester.

Exemplary PKC inhibitors included within the scope of the present invention include, but are not limited to, the following compounds:

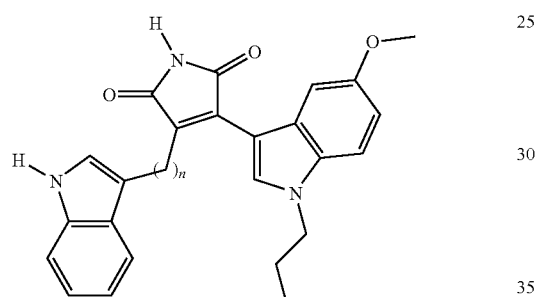

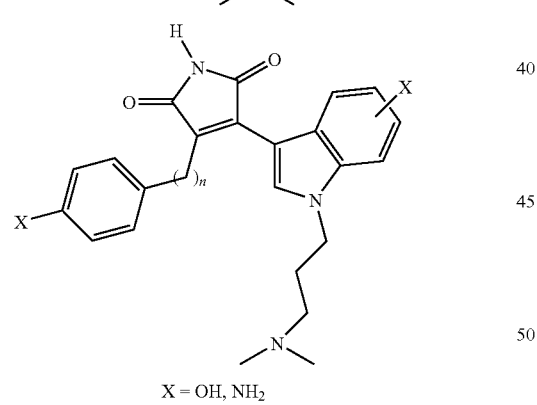

X = OH, NH$_2$

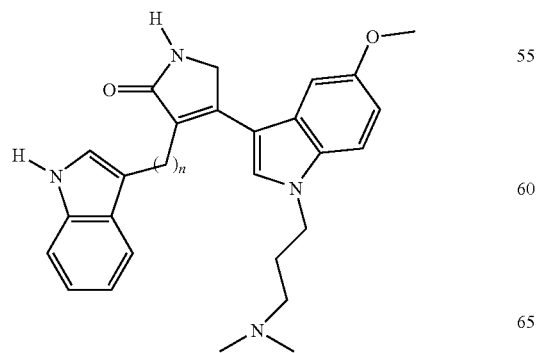

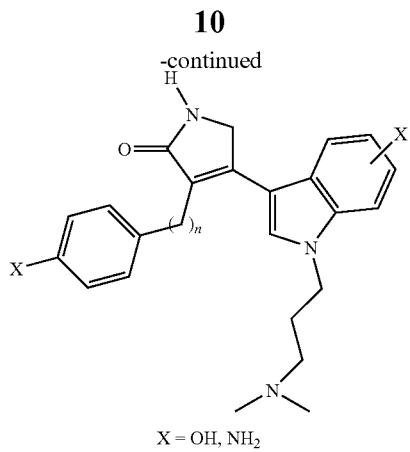

X = OH, NH$_2$

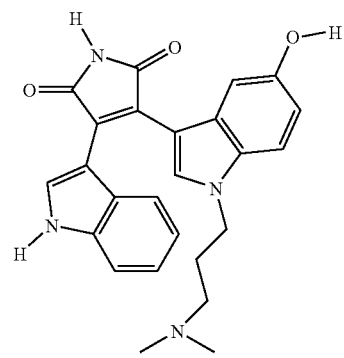

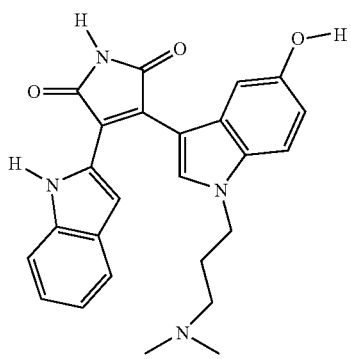

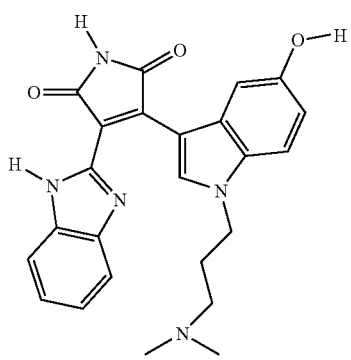

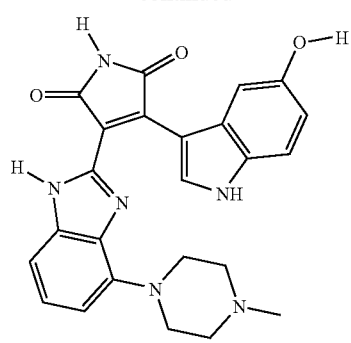
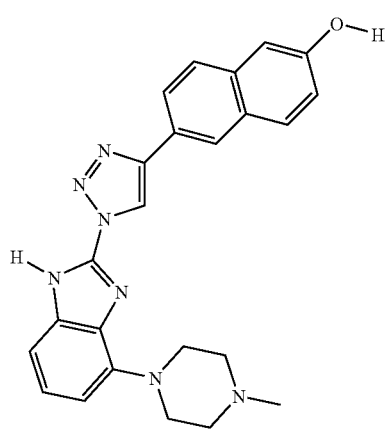
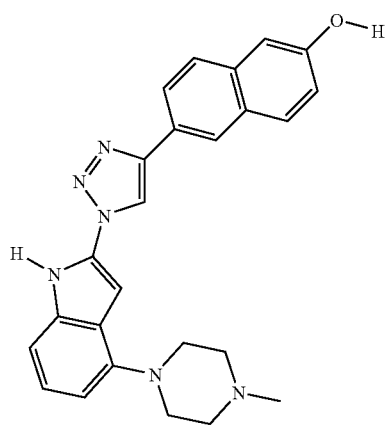
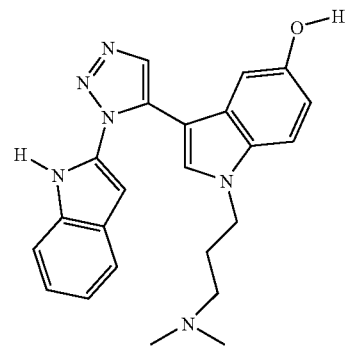
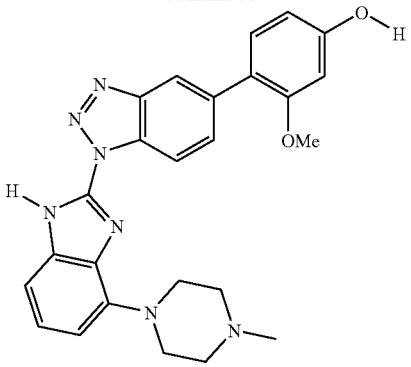
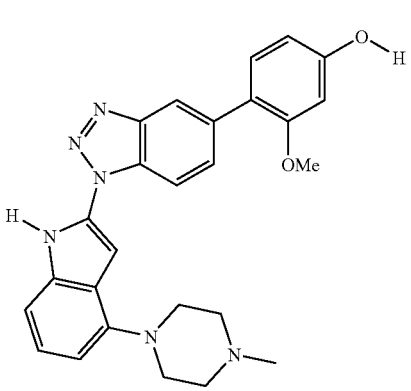
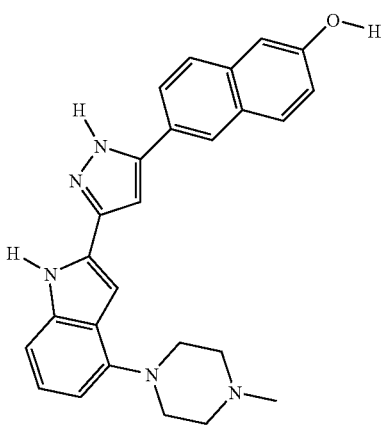
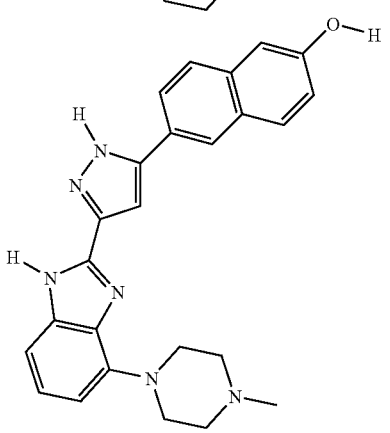

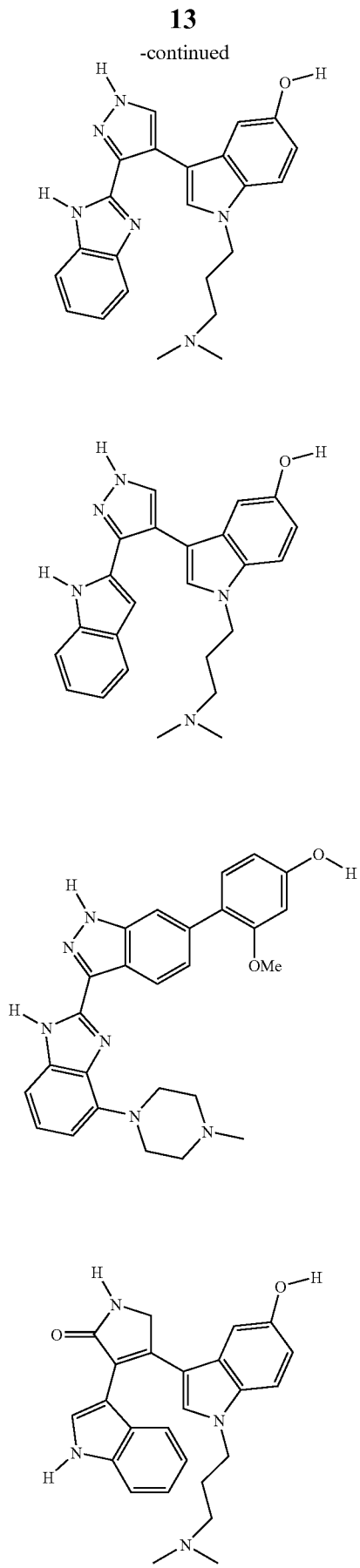
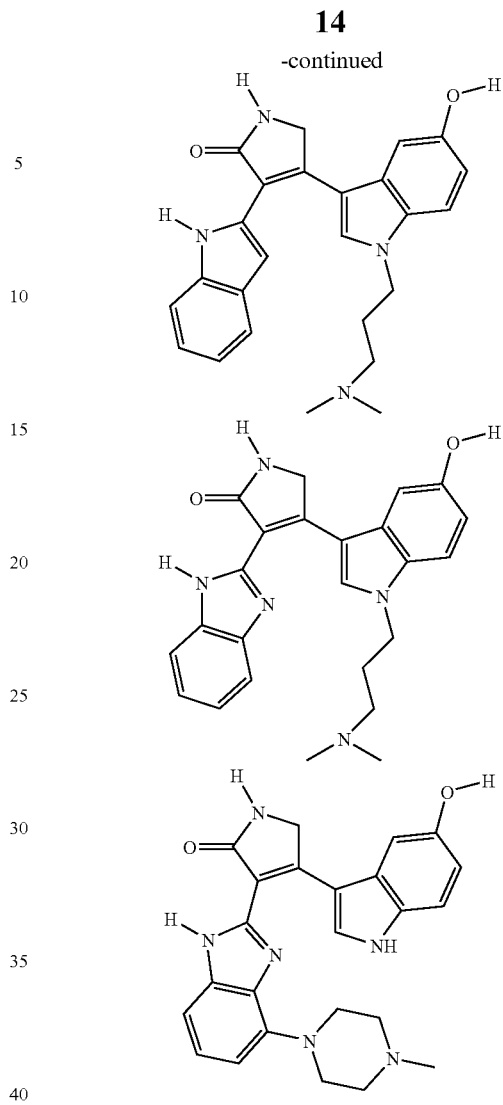

PKC inhibitors disclosed herein can be prepared using synthetic approaches routinely practiced in the art based upon the synthesis of structurally similar compounds.

As demonstrated herein, inhibitor concentrations of ≧2.5 µM were sufficient to establish and maintain stem cells in the undifferentiated state. Accordingly, particular embodiments of the invention embrace use of the selective PKC inhibitor in the range of 100 nm to 5 µM, or more desirably in the range of 1 µM to 3 µM.

Stem cells established and maintained in accordance with the present invention find application in experimental, therapeutic and prophylactic treatment of various diseases or conditions in a human or animal. Such diseases or conditions include, but are not limited to, Parkinson's, Alzheimer's, Multiple Sclerosis, spinal cord injuries, stroke, macular degeneration, burns, liver failure, heart disease, diabetes, Duchenne's muscular dystrophy, osteogenesis imperfecta, osteoarthritis, rheumatoid arthritis, anemia, leukemia, breast cancer, solid tumors, and AIDS.

Once established, propagated and expanded, stem cells of the invention can be exposed to a variety of soluble factors to induce differentiation. For example, IL-3 directs cells to become macrophages, mast cells or neutrophils (Wiles & Keller (1991) *Development* 111:259-267); IL-6 directs cells to the erythroid lineage (Biesecker & Emerson (1993) *Exp.*

Hematol. 21:774-778); retinoic acid induces neuron formation (Stager, et al. (1993) *Dev. Genet.* 14:212-224; Bain, et al. (1995) *Dev. Biol.* 168:342-357); transforming growth factor (TGF-beta 1 induces myogenesis (Rohwedel, et al. (1994) *Dev. Biol.* 164:87-101), TGF-beta 1 and activin-A induce differentiation of muscle cells; retinoic acid, bFGF, BMP-4, and EGF induce differentiation of ectodermal and mesodermal cells; while NGF and HGF allow differentiation of cells from all three germ layer lineages (Schuldiner, et al. (2000) *Proc. Natl. Acad. Sci. USA* 97(21):11307-12).

In so far as the instant methods of establishing and maintaining stem cells are easy and cost effective, it is contemplated that the present invention can be used to maintain mammalian ES and iPS cells for regular research purposes, generate new stem cell lines from mice and other mammalian species for stem cell banking, and efficiently generate, propagate, and maintain iPS cells from patients for regenerative medicine and research purposes. Indeed, the instant methods will be useful in stem cell banking and in the generation of patient-specific iPS cells.

The invention is described in greater detail by the following non-limiting examples.

EXAMPLE 1

Experimental Procedures

Inhibitors. Gö6983 was purchased from three different companies (Sigma, St. Louis, Mo.; EMD Chemicals Inc.; and Tocris Biosciences) for validation. In all experiments except the concentration profile, Gö6983 was used at 5 µM final concentration. Gö6976 (0.1-2 µM) was purchased from Sigma. Rottlerin (0.1-5 µM), and RO-318425 (0.1-5 µM) were purchased from EMD Chemicals. Jak Inhibitor I (10 µM), PD0325901 (1 µM) and AKT inhibitor IX (10 µM) were from Calbiochem and CHIR99021 (3 µM) was purchased from Stemgent.

ES Cell Cultures. E14, R1, Stat3$^{-/-}$, Ezh2$^{-/-}$, and Eed--/-- ES cells were used in this study. Cells maintained for 5 days under different culture conditions were used for immunofluorescence study while for other purposes, they were analyzed under steady state condition, i.e., within 8-12 hours of LIF and other inhibitor treatment. Detailed experimental protocol for ES cell culture under different experimental conditions is described herein.

E14 ES Cell Cultures. Cells were grown in ES-IMDM media (Lonza, Walkersville, Md.) in a feeder-free condition. ES-IMDM was supplemented with 15% serum, $10^5$ U/100 ml of LIF (ESGRO, Millipore, Calif.) and 0.0124% monothioglycerol (MTG; Sigma Aldrich). Cells were grown for 3-5 days with change of medium every day. For inducing differentiation in monolayer culture and to determine the effect of Gö6983 in preventing differentiation, E14 cells were cultured on gelatin-coated plastics for 8 days without LIF. Details of experiments performed at clonal-density are described herein. To maintain E14 cells with Gö6983, serum supplemented ES-IMDM was used in the presence of 5 µM Gö6983 and was passed after every 3-5 days. For all assays involving elucidation of different signaling mechanism responsible for maintenance of pluripotency, cells from a ~70% confluent ES culture plate were washed two times with 1× phosphate-buffered saline (PBS), trypsinized and plated on a 6-well tissue culture plate and treated with or without LIF or Gö6983 or different inhibitors for ~10 hours followed by preparation of protein lysates and RNA. The PKCζ knockeddown E14 cells that were generated in this study were maintained in serum supplemented ES-IMDM on gelatin-coated plates in the absence of Gö6983 or LIF or any other inhibitor and passed after 3-5 days. For the experiments herein, cells were continuously cultured at least for 5 consecutive passages (>18 days) on gelatin-coated plates without significant differentiation.

Quantitative Clonal Assay. ES and iPS cells were dissociated into single cells using 0.05% trypsin/EDTA and 2-20 cells were plated on each well of a 96-well culture plate. The cells were cultured for 6-7 days, colonies were stained for Nanog, and the number of Nanog positive colonies was counted. For determining maintenance of self-renewal for multiple passages at clonal density with Gö6983, E14 cells were cultured at clonal density in 96 well plates with Gö6983; cells from undifferentiated colonies were trypsinized after day 6, and again plated at clonal density with Gö6983. This procedure was repeated for five consecutive passages (>30 days).

Embryoid Body (EB) Formation. To generate EBs, ES cells were grown in absence of LIF in ES-IMDM differentiation media containing 15% FBS, selected for endothelial cell differentiation (Stem Cell Technologies, Vancouver, BC), 1% L-glutamine, 1% ascorbic acid (Stem Cell Technologies, Ocala, Fla.), and 3 µl/ml MTG. Cells were trypsinized and were made into single cell suspensions, and washed to completely remove LIF. To generate day 4.5 EBs, 4000 cells/ml were added to ES-IMDM differentiation media.

ES Cell Differentiation on Collagen-IV and With Retinoic Acid. To differentiate ES cells in monolayer culture on collagen IV, around $3 \times 10^4$ cells per well were transferred to collagen IV-coated 6-well plates (BD Biosciences, Franklin Lakes, N.J.) cultured for 5 days in ES differentiation medium containing DMEM (Invitrogen), 15% FBS (selected for endothelial differentiation, Stem Cell Technologies, Vancouver, BC), sodium pyruvate and L-glutamine with or without LIF and Gö6983, and were recovered by cell dissociation buffer (BD Biosciences, Franklin Lakes, N.J.). For culturing multiple passages with Gö6983 on collagen-IV, the recovered cells were again plated at a density of $\sim 3 \times 10^4$ cells per well and cultured again for 5 days. For the experiments herein, E14 cells were continuously cultured with Gö6983 (without LIF) up to 8 consecutive passages on collagen IV plates without any noticeable differentiation. Besides, E14 cells maintained on collagen IV with Gö6983 for 7 consecutive passages efficiently generated chimeras. For RA-induced differentiation on monolayer culture, ES cells were treated with all-transretinoic acid (Sigma, St. Louis, Mo.) in ethanol at a concentration of 1 µM with or without LIF and Gö6983 for 6 days followed by study of expression of pluripotency markers (by immunofluorescence or western blot or RT-PCR analysis).

Growth Under Serum Free Condition. E14 cells were maintained in serum-free N2B27 medium containing DMEM/F12 (Invitrogen), Neurobasal media (Invitrogen), B27 supplement (Invitrogen), N2 supplement (Invitrogen), BSA fraction V (Invitrogen), 2-mercaptoethanol (Sigma) and LIF/BMP4 (R&D Systems, Minneapolis, Minn.) with change of medium on alternate days and passed in every 2-4 days. For experiments with Gö6983, $\sim 5 \times 10^4$ E14 cells were plated on each well of a gelatin-coated 6-well plate having N2B27 medium without LIF/BMP4 and with or without 5 µM Gö6983 and cultured for 3-4 days before passing. Cells were analyzed for expression of different markers (by RT-PCR or immunofluorescence study). For experiments at clonal density, initially, E14 cells were cultured at high density in N2B27 medium with Gö6983 alone for 4 passages, then ~200 cells were plated in each wells of a 96-well plate with Gö6983 in N2B27 and cultured for 7 more days. After 7 days, colonies were analyzed for Oct4 staining.

R1 ES Cells. R1 Cells were maintained on MEF feeder in ES-IMDM media supplemented with 15% ES-cell quality serum, $10^5$ U/100 ml of LIF. Cells were grown for 3-5 days with change of medium every day. For inducing differentiation in monolayer culture and to determine the effect of Gö6983, cells were cultured at feeder-free condition and without LIF for 7 days.

Ezh2$^{-/-}$ ES Cells. Ezh2$^{-/-}$ cells, passage 6, were maintained on irradiated MEF feeders in standard ES medium (DMEM; Dulbecco's modified Eagle's medium) supplemented with 15% heat-inactivated fetal calf serum, 0.1 mM 2-mercaptoethanol, 2 mM L-glutamine, 0.1 mM non-essential amino acid, 1% of nucleoside mix (100× stock, Sigma), 1000 U/ml LIF and 50 U/ml Penicillin/Streptomycin. For experiments involving Gö6983, Ezh2$^{-/-}$ cells were passed once without feeders and used for subsequent analysis. For experiments on collagen IV, ~3×10$^4$ Ezh2$^{-/-}$ cells were plated in each well of a six-well tissue culture plate in the presence or absence of LIF and Gö6983.

Eed$^{-/-}$ ES Cells. Eed$^{-/-}$ ES cells, passage 4, were maintained in same medium as mentioned for Ezh2$^{-/-}$ cells but supplemented with extra LIF (2000 U/ml) to suppress spontaneous differentiation. For experiments with Gö6983, Eed$^{-/-}$ cells were passed one time without feeders and treated similar to Ezh2$^{-/-}$ cells as mentioned above.

Stat3$^{-/-}$ ES Cells. Passage 12 Stat3$^{-/-}$ ES cells were maintained on N2B27 medium with 1 µM PD0325901 and 3 µM CHIR99021 and passaged every 3-4 days. For studies involving Gö6983, around 1-2×10$^4$ cells were plated on 6-well plates having N2B27 medium with or without 5 µM Gö6983 and analyzed for the expression of pluripotency markers.

Quantitative RT-PCR Analysis. RNA was extracted from different cell samples with TRIZOL reagent (Invitrogen). cDNA was prepared by annealing RNA (1 µg) with 250 ng of a 5:1 mixture of random and oligo(dT) primers heated at 68° C. for 10 minutes. This was followed by incubation with Moloney murine leukemia virus reverse transcriptase (50 units) (Invitrogen, Carlsbad, Calif.) combined with 10 mM DTT, RNasin (PROMEGA, Madison, Wis.), and 0.5 mM dNTPs at 42° C. for 1 hour. Reactions were diluted to a final volume of 100 µl and heat inactivated at 97° C. for 5 minutes. Twenty µl PCR reactions contained 2 µl cDNA, 10 µl SYBR Green Master Mix (Applied Biosystems, Foster City, Calif.) and corresponding primer sets. Relative expression levels were determined from a standard curve of serial dilutions of proliferating ES cell cDNA samples and were normalized to the expression of glyceraldehyde-3-phosphate dehydrogenase (GAPDH). At least three independent experiments were done for each set of data. Primers used in this study are listed in Table 2.

TABLE 2

| Gene (Mouse Specific) | | Primers | SEQ ID NO: |
|---|---|---|---|
| Oct4 | Forward | CTCACCCTGGGCGTTCTCT | 1 |
|  | Reverse | AGGCCTCGAAGCGACAGA | 2 |
| Nanog | Forward | TGCTACTGAGATGCTCTGCACA | 3 |
|  | Reverse | TGCCTTGAAGAGGCAGGTCT | 4 |
| Sox2 | Forward | GCACATGAACGGCTGGAGCAACG | 5 |
|  | Reverse | TGCTGCGAGTAGGACATGCTGTAGG | 6 |
| Gata4 | Forward | CCCTGGAAGACACCCCAAT | 7 |
|  | Reverse | TGGACATGGCCCCACAAT | 8 |
| Gata6 | Forward | AGATGAATGGCCTCAGCAGG | 9 |
|  | Reverse | CAAGCCGCCGTGATGAA | 10 |
| Nestin | Forward | CTGCAGGCCACTGAAAAGTT | 11 |
|  | Reverse | AGGTGTCTGCAAGCGAGAGT | 12 |
| Brachyury | Forward | CCAACCTATGCGGACAATTCATCTGC | 13 |
|  | Reverse | GTGTAATGTGCAGGGGAGCCTCGAA | 14 |
| Cdx2 | Forward | GGACTGGAGCATGTATCCTAGCT | 15 |
|  | Reverse | TAACCACCGTAGTCCGGGTACT | 16 |
| Rex1 | Forward | GGCAGTTTCTTCTTGGGATTT | 17 |
|  | Reverse | GCGATCCTGCTTTCTTCTGT | 18 |
| Pax6 | Forward | AACACCAACTCCATCAGTTC | 19 |
|  | Reverse | ATCTGGATAATGGGTCCTCT | 20 |
| Gsc | Forward | GAAGCCCTGGAGAACCTCTT | 21 |
|  | Reverse | TCGACTGTCTGTGCAAGTCC | 22 |
| Cxcr4 | Forward | TCCAACAAGGAACCCTGCTTC | 23 |
|  | Reverse | TTGCCGACTATGCCAGTCAAG | 24 |
| Plaur | Forward | TCATCAGCCTGACAGAGACC | 25 |
|  | Reverse | AGGTGCAGGACGCACACTC | 26 |
| Vim | Forward | AGGAGGCCGAGGAATGGT | 27 |
|  | Reverse | CATCGTTGTTCCGGTTGG | 28 |
| Igfbp2 | Forward | CCCCTGGACATCTCTACTCC | 29 |
|  | Reverse | GGGTTCACACACCAGCACTC | 30 |
| Id1 | Forward | CTGAACGGCGAGATCAGTG | 31 |
|  | Reverse | CTCCTGAAGGGCTGGAGTC | 32 |
| Id2 | Forward | GGACATCAGCATCCTGTCCT | 33 |
|  | Reverse | CTCCTGGTGAAATGGCTGAT | 34 |
| Id3 | Forward | CAGGTGGTCCTGGCAGAG | 35 |
|  | Reverse | GAGAGAGGGTCCCAGAGTCC | 36 |
| Gapdh | Forward | TGCCCCCATGTTTGTGATG | 37 |
|  | Reverse | TGTGGTCATGAGCCCTTCC | 38 |

Western Blot Analysis. Whole cell lysates were prepared in SDS-gel loading buffer and resolved by 10% PAGE. The antibodies used for this study included β-actin Clone AC-15 from Sigma; p-STAT3 (Tyr705), p-p44/42 MAPK (tyr202/tyr204), p44/42 MAPK, GSK3β, Phospho Akt (Ser473), Akt, p-NFκβ p65 (Ser536), c-Myc, p-c-Myc (Thr58/Ser62), p-p90RSK (Thr359/Ser363), RSK1, Suz12 (D39F6), and Ezh2 (AC22) from Cell Signaling Technology; STAT3 (C-20), Oct-4 (C-10), Nanog (M-149), PKC α (C-20), PKC βI (C-16), PKC βII (C-18), PKC γ (C-19), PKC δ (C-20), PKC ζ (c-20), p-PKC ζ (Thr 410)-R, p-NFκβ p65 (ser311), and RelA (p65) from Santa Cruz Biotechnology; p-LGL1/LGL2 (S650/S654), SSEA4 and H3K4Me3 from Abcam; LGL2 (M06), clone 4G2 from Abnova; β-Catenin from BD Transduction Laboratories, and H3K27Me3 and H3K9Me3 from Millipore.

Immunostaining. Immunostaining of Oct4, and Nanog expression was performed using standard protocols. Briefly, ES cells were fixed in 4% paraformaldehyde/4% sucrose, permeabilized with 0.1% TRITON X 100 (Sigma). Cells were blocked by adding 1% fish gelatin (Sigma, St. Louis, Mo.) and incubated overnight at 4° C. with 200 µl of primary antibodies. Fluorescent-conjugated secondary antibodies (ALEXA FLUOR 488, and ALEXA FLUOR 568, Molecular Probes, Invitrogen) were used at 1:250 dilutions to visualize cells. Images were captured using a LEICA fluorescence microscope.

Cell Proliferation Assay. E14 ES cells were seeded and incubated for 2 days in the presence of different concentrations of Gö6983. Cell proliferation was measured with CELLTITER 96 AQUEOUS One Solution Reagent (Promega, Madison, Wis.) following the manufacturer's protocol.

Cytosolic β-Catenin Stabilization Assay. ES cells were treated with Wnt3A-conditioned medium or Gö6983 or LIF for 10 hours, and lysed hypotonically on ice with 1× TE (pH 7.4) with protease inhibitors. Lysates were centrifuged at 100,000 g at 4° C. for 45 minutes to collect and analyze cytosolic fractions.

TOPFLASH Luciferase Reporter Assay. 514 cells were transfected with 0.5 µg of SUPER8XTOPFlash and 20 ng of phRL Renilla luciferase vectors per well using LIPO-FECTAMINE (Invitrogen). Transfected cells were cultured with or without LIF, or Wnt3a-conditioned medium, or with Gö6983, and luciferase activity was measured after 48 hours of transfection using Dual-Luciferase Reporter Assay System (Promega).

Analysis of NF-κB5X-Luc Reporter Activation. E14 ES or PKCζkd cells (2-4×10⁴) were seeded on 24-well plates for hours. Cells were transfected with 1 µg of plasmid (PATH-DETECT NF-kB cis-Reporting System, Stratagene) in OPTI-MEM. Transfection mixture was removed after 5 hours with appropriate media. Luciferase activity was measured 24 hours post-transfection and expressed relative to total protein present in the whole cell lysate.

Quantitative ChIP Assay. Real-time PCR-based quantitative ChIP analysis was performed according to known methods (Dutta, et al. (2008) supra). Proliferating E14 cells (+LIF), ES cells differentiated on Collagen-IV with or without Gö6983 were either trypsinized or collected by using cell-dissociaton buffer and protein-DNA crosslinking was conducted by treating cells with formaldehyde at a final concentration of 1% for 10 minutes at room temperature with gentle agitation. Glycine (0.125 M) was added to quench the reaction. Antibodies against EZH2, SUZ12, H3K27Me3, H3K9Me3, and H3K4Me3 were used to immunoprecipitate protein-DNA crosslinked fragments. Immunoprecipitated DNA was analyzed by real-time PCR (ABI 7500, Applied Biosystem, Foster City, Calif.). Samples from three or more immunoprecipitates were analyzed using a standard curve from sonicated total chromatin (input) samples. Gene-specific primers that are used for quantitative PCR are listed in Table 3.

TABLE 3

| Gene | | Primer Sequence | SEQ ID NO: |
|---|---|---|---|
| Nanog | Forward | TTGGGACCAGCTAGAGCAAT | 39 |
| | Reverse | CCAGGCTTGTCTACCACCAT | 40 |
| Oct4 | Forward | TGGGCTGAAATACTGGGTTC | 41 |
| | Reverse | TTGAATGTTCGTGTGCCAAT | 42 |
| Sox2 | Forward | CCTAGGAAAAGGCTGGGAAC | 43 |
| | Reverse | GTGGTGTGCCATTGTTTCTG | 44 |
| GATA6 | Forward | CCTTCCCATACACCACAACC | 45 |
| | Reverse | CCCCTCCTTCCAAATTAAGC | 46 |

TABLE 3-continued

| Gene | | Primer Sequence | SEQ ID NO: |
|---|---|---|---|
| Gsc | Forward | CGTCCGCCTTCGTACAAGTTGTCT | 47 |
| | Reverse | GTGTTAGGAGCTAGGGAGAGTCAGG GTAG | 48 |
| Olig2 | Forward | GCGATTGTCTCACTTCTTTCTCCACAC | 49 |
| | Reverse | AGGCTGGCGTCCGAGTCCAT | 50 |
| Pax6 | Forward | ATTTGGAAACAAACGCCCTA | 51 |
| | Reverse | AGGGAACACACCAACTTTCG | 52 |
| Sox17 | Forward | CCACTCACTCTGAGGCTCGCTGTAG | 53 |
| | Reverse | CCAAAGCAGACCTGAGGCTCGAA | 54 |

RNA Interference and Rescue of PKCζ Expression in RKCζkd Cells. Lentiviral vectors containing short hairpin RNAs (shRNAs) targeting mouse PKCζ mRNA were cloned in pLKO1 (Open Biosystems, Huntsville, Ala.). Lentiviral supernatants were produced in HEK-293T cells according to known methods (Dutta, et al. (2008) supra). E14 cells were transduced with lentiviral supernatants and were selected by the addition of 1 µg/ml of puromycin (Sigma). Construct with target sequence 5'-ATC CCG GTA AGT TCT GTT G-3' (SEQ ID NO:55), corresponding to the 3'-UTR region of PKCζ mRNA, specifically knocked-down PKCζ expression. For rescue of PKCζ expression, PKCζkd cells were re-infected with lentiviral particles having PKCζ cDNA (subcloned from plasmid pMTH PKCζ, Addgene) into the pLKO.3G vector (Addgene) under a hU6 promoter and selected by the expression of EGFP, which is expressed from the same vector under the control of an hPGK promoter). Another construct with target sequence 5'-GGA CCT CTG TGA GGA AGT G-3' (SEQ ID NO:56, shRNA2), corresponding to the amino acid coding region of PKCζ mRNA, also specifically knocked-down PKCζ.

DNA Methylation Analysis. One µg of genomic DNA was subjected to bisulfite treatment using CPGENOME Fast DNA Modification Kit (Chemicon Int.). For bisulfite sequencing, the modified DNA was amplified by nested polymerase chain reaction (PCR) using two forward (F) primers and one reverse (R) primer: Oct4 (F1, 5'-GTT GTT TTG TTT TGG TTT TGG ATA T-3', SEQ ID NO:57; F2, 5'-ATG GGT TGA AAT ATT GGG TTT ATT TA-3', SEQ ID N:58; and R, 5'-CCA CCC TCT AAC CTT AAC CTC TAA C-3', SEQ ID NO:59) and Nanog (F1, 5'-GAG GAT GTT TTT TAA GTT TTT TTT-3', SEQ ID NO:60; F2, 5'-AAT GTT TAT GGT GGA TTT TGT AGG T-3', SEQ ID NO:;61; and R, 5'-CCC ACA CTC ATA TCA ATA TAA TAA C-3', SEQ ID NO:62). The resulting PCR product was gel purified, subcloned into pGEM-T vector (Promega) and sequenced using M13R primer. Following primers were used for MSP: Oct4, (F) 5'-GGT TTT AGA AAT AAT TGG TAT ACG A-3' (SEQ ID NO:63), and (R) 5'-CTA TTA ACA CTA CAC CCT CTC GAC-3' (SEQ ID NO:64); and Nanog, (F) 5'-ATT TGT GAG TAT AAG GAT TGA TCG G-3' (SEQ ID NO:65), and (R) 5'-TTT CTT TAA AAT AAA ATT TCA CGT A-3' (SEQ ID NO:66). PCR products were analyzed on agarose gel.

De Novo Derivation of New ES Cells With Gö6983. Blastocysts from 6-week-old female 12952/SvPasCrl (129/Sv) strain mice (Charles River Laboratory, Wilmington, Mass.) were isolated at 3.5 day post-coitum. Isolated blastocysts were plated on gelatin-coated plastic in medium containing Gö6983 and FBS and without LIF. To obtain ES cell colonies, blastocyst outgrowths were disaggregated with trypsin and replated on gelatin-coated wells with Gö6983 and FBS. ES cell colonies were expanded by replating with Gö6983 at clonal or higher density. For in vitro analysis, cells were differentiated following the same protocol described herein. After six passages with Gö6983-condition, chromosome numbers were checked by karyotyping, and injected in C57BL/6 blastocysts for chimera generation.

Generation of iPS Cells. iPSCs were derived using lentiviral vectors (STEMGENT), expressing four mouse transcription factors (Oct4, Sox2, Klf4 or c-Myc) under the control of the doxycycline (Dox)-inducible tetO operator. 129/Sv MEFs were infected with viral mix following manufacturer's protocol. Twenty hours post-transduction, cells were reseeded in ES cell growth medium with either LIF or Gö6983 at a density of $5 \times 10^4$ cells per well of a 6-well plate and treated with Dox (2 µg/ml) for 48 hours. To determine the phenotype of the iPS colonies, expression of two pluripotency markers, Nanog and Rex-1, were analyzed. For further analysis, each visible iPS colony was manually picked, trypsinized, cells were replated at clonal and higher density in medium with Gö6983 and the expression of pluripotent markers were confirmed by RT-PCR and immunofluorescence. For chimera generation, cells from two different iPS clones were propagated at clonal density with Gö6983, expanded for four passages and were injected into blastocysts.

Chimera Generation and Germ-Line Transmission. Prepubertal (3 weeks of age) donor C57BL/6 female mice (Jackson Laboratory, Bar Harbor, Me.) were superovulated, mated overnight to intact C57BL/6 stud males and euthanized by cervical dislocation on day 3.5. Uteri were collected after euthanasia and flushed with M2 medium (Millipore, Bilerica, Mass.) for the collection of blastocysts. Eight to ten ES or iPS cells were injected into the blastocoel of each blastocyst. After injection, the blastocysts were surgically transferred into recipient females that were pseudopregnant by mating with vasectomized males. Recipient females carried the pups to term and nursed until weaning at three weeks. High-level chimeras, generated from newly derived ES cells, were mated with C57BL/6 adult mice to test for germline transmission.

Table 4 lists the number of chimeric mice that were obtained from Gö6983-treated/derived.

TABLE 4

| Type of ES cell | Blastocyst injected # | Pups # | Chimera # | # of Chimera showing Germline Transmission |
|---|---|---|---|---|
| E14 | 59 | 7 | 5 | na |
| ES 1** | 45 | 15 | 5 | 3 |
| ES 2** | 38 | 6 | 2 | 2 |
| iPSC 1 | 18 | 5 | 3 | na |
| iPSC 2 | 30 | 6 | 3 | Na |

**ES cell line that was derived with Go6983.
Na, not available.

EXAMPLE 2

Inhibition of PKC Signaling by Gö6983 is Sufficient to Maintain Pluripotent State of Mouse ES Cells ES cells deal with two critical, yet opposing forces; to maintain a pluripotent state with self-renewal ability and the ability to respond to d'fferentiation signals. Thus, understanding the molecular mechanisms that maintain the pluripotent states of ES cells and dictates differentiation to a particular cell lineage of particular interest. Since the establishment of first ES cell line, several culture conditions have been established to maintain the pluripotent state of ES cells. Activation of STAT3 by cytokine LIF is a primary strategy to maintain the pluripotent culture of mouse ES cells. However, recent studies have indicated that pharmacological blockage of differentiation signaling, induced by fibroblast growth factor 4 (FGF4) and mitogen-activated protein kinase (MAPK), can maintain the pluripotency and self-renewal ability of rodent ES cells. In addition, it has also been demonstrated that inhibition of glycogen synthase kinase 3-Wnt signaling maintains the pluripotent states of both mouse and human ES cells. These strategies have lead to the identification of a core transcription factor network that is sufficient for establishing and maintaining the epigenetic mechanisms required for the pluripotent state of stem cells.

Under proper growth conditions, like withdrawal of LIF from the culture medium, altered gene expression patterns are induced leading to differentiation of ES cells. In the absence of LIF, ES cells can be differentiated to three-dimensional embryoid bodies (EBs), which contain cells of three germ layers; endoderm, mesoderm and ectoderm. However, more skewed differentiation of mouse ES cells can also be obtained with additional treatment along with the absence of LIF. For example, culturing ES cells on collagen IV without LIF strongly induces mesodermal differentiation.

Pharmacological inhibition of PKC signaling by a selective PKC inhibitor Gö6983 (selective inhibitor of PKC isoforms $\alpha$, $\beta$, $\gamma$, $\delta$, $\zeta$ and $\mu$) inhibits angiogenic signal-induced VEGFR1 expression in endothelial cells (Dutta, et al. (2008) *J. Biol. Chem.* 283:25404-25413). The PKC family is involved in multiple signaling pathways and is composed of multiple serine/threonine protein kinases that are divided into three subfamilies; (i) classical PKCs (isoforms $\alpha$, $\beta1$, $\beta2$ and $\gamma$, Calcium and phospholipid-dependent), (ii) novel PKCs (isoforms $\delta$, $\epsilon$, $\eta$ and $\theta$, calcium-independent and phospholipid-dependent), and (iii) atypical PKCs (isoforms $\zeta$ and $\zeta/\iota$ and $\mu$). PKC isoforms have been studied during ES cell differentiation (Heo & Han (2006) *Stem Cells* (Dayton, Ohio) 24:2637-2648; Prudhomme, et al. (2004) *Proc. Natl. Acad. Sci. USA* 101:2900-2905; Wang, et al. (2005) *J. Biol. Chem.* 280:26415-26424; Zhou, et al. (2003) *Dev. Biol.* 255:407-422). However, the involvement of the PKC signaling pathway in ES cell pluripotency is not described in the art. As PKC signaling altered angiogenic signal-mediated gene expression pattern in endothelial cells, it was contemplated that the Protein Kinase C signaling might be involved in regulating gene expression pattern during formation of the endothelial cell lineage. During development, endothelial cells are developed from the Flk1+ mesodermal progenitors. Therefore, the role of Protein Kinase C signaling on the formation of Flk1+ mesodermal cells was determined using a mouse ES cell differentiation model.

Figure 1B:
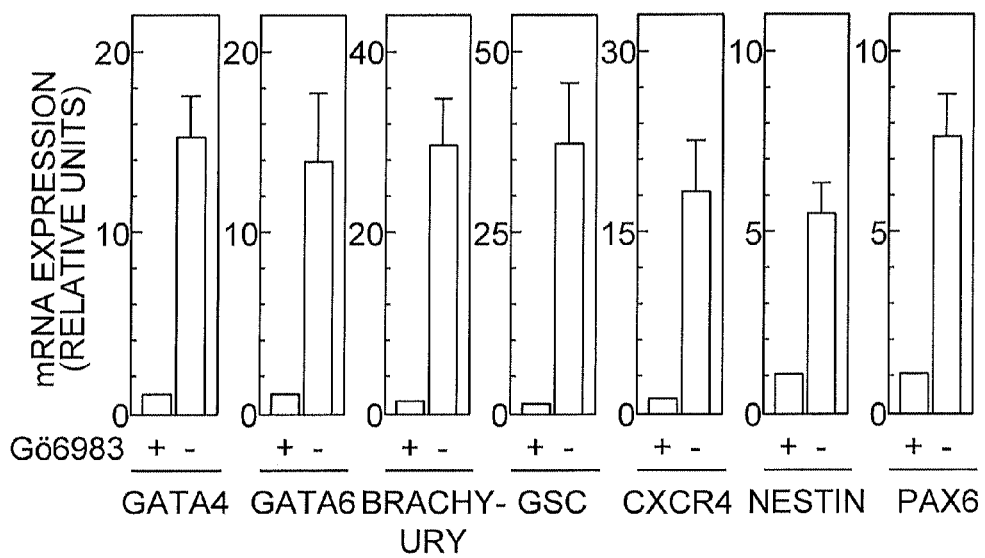

During this analysis it was observed that when cultured with Gö6983 in the absence of LIF, ES cells did not differentiate and maintained their undifferentiated colony morphology. Concentration profile analysis showed that Gö6983 efficiently maintained undifferentiated ES cell colony at a concentration of ≧2.5 µM. Quantitative RT-PCR analysis showed that when treated with Gö6983, ES cells maintained the expression of pluripotency markers including Oct4, Nanog, Sox2 and Rex-1 (FIG. 1A). In addition, the induction of developmental genes, which are required for lineage commitment, did not occur (FIG. 1B). As PKC signaling is involved in cell proliferation and survival in multiple contexts, the effect of Gö6983 on ES cell proliferation was analyzed. This analysis indicated that at 2.5 µM concentration of Gö6983, which almost completely inhibited ES cell differentiation, cell proliferation was inhibited only by ~30%. However, no significant loss in ES cell survival at clonal density was observed even at ≦10 µM concentration of Gö6983. These results indicate that culturing mouse ES cells with Gö6983, in the absence of LIF, maintains their self-renewal ability without any significant effect on the cell viability.

Initial experiments were conducted with the E14Tg2a (E14) ES cell line that can be maintained in undifferentiated state without MEF feeder layer. To test whether the Gö6983-mediated effect was independent of mouse ES cell line, R1 ES cells, which are normally maintained in the presence of LIF on MEF, were analyzed. It was found that, like E14 ES cells, treatment with Gö6983 replaced the requirement of LIF and MEF to maintain and propagate undifferentiated R1 ES cells.

Figure 1C:
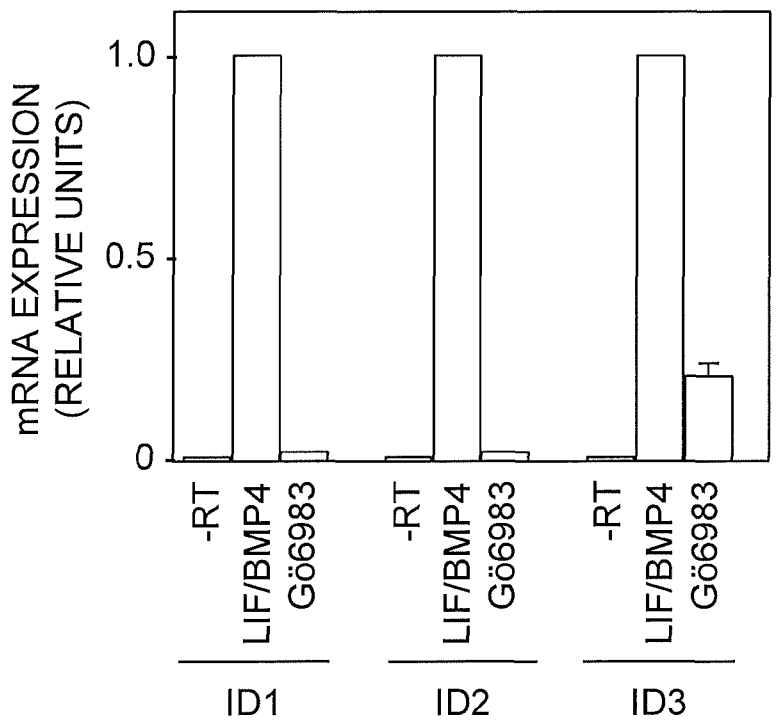

In addition, tests with ES cell medium containing different batches of fetal bovine serum from different sources showed that Gö6983 maintained ES cell pluripotency in all culture media irrespective of serum source. The effect of Gö6983 on ES cell survival and differentiation was also tested in the absence of serum. It was found that, when grown in N2B27 medium (Ying, et al. (2003) *Cell* 115:281-292) without serum, LIF, and BMP4, mouse ES cells could be maintained in an undifferentiated state and this maintenance was not associated with the induction of inhibitor-of-differentiation genes (FIG. 1C). Although undifferentiated colonies in N2B27 medium plus Gö6983 were obtained, in general, cell survival was poor when propagated at clonal density, indicating a compromise of cell viability but not the self-renewal.

Figure 1D:
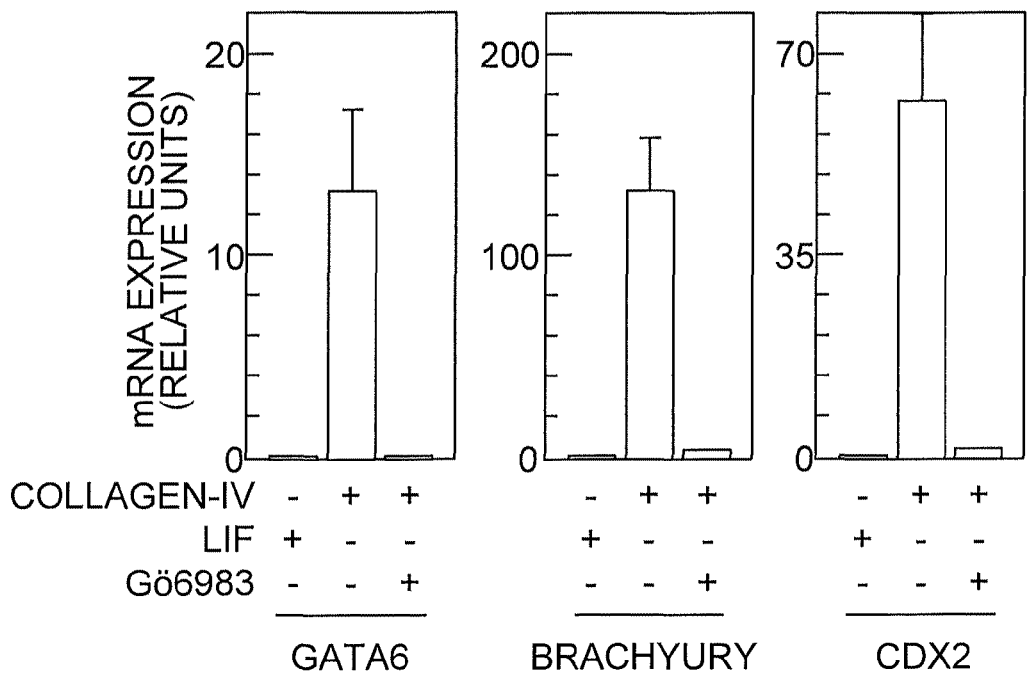
Figure 1E:
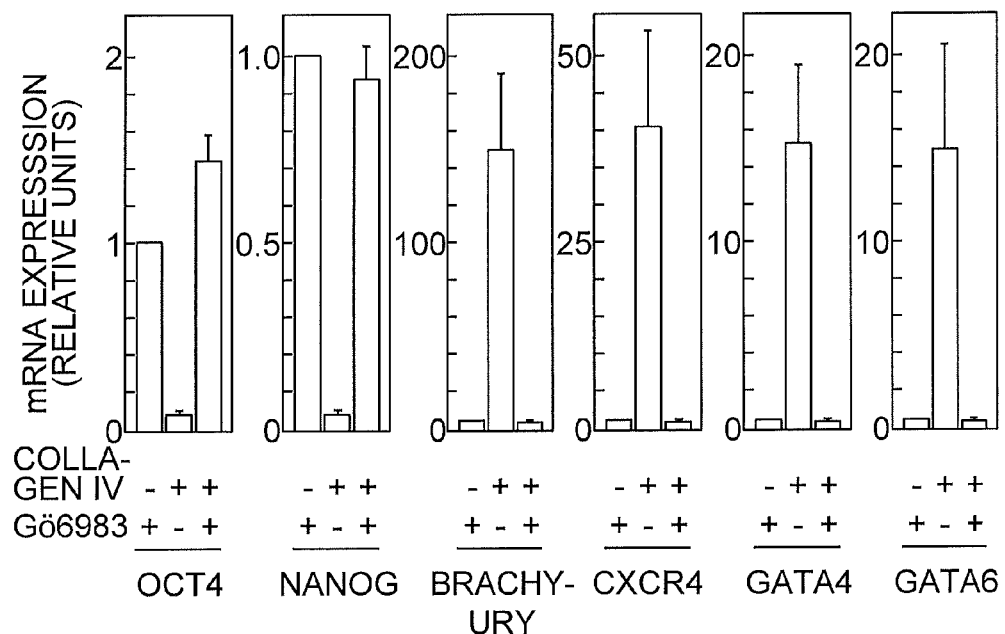

To determine whether Gö6983 inhibits mouse ES cell differentiation under other differentiating culture conditions, ES cell differentiation was analyzed in the presence of collagen IV or retinoic acid, in the absence of LIF. These results indicated that Gö6983 inhibited ES cell differentiation under these culture conditions. A test with MAP kinase inhibitor U0216 and PI3 kinase inhibitor Ly294002 showed that they failed to block differentiation of ES cells on collagen IV in the absence of LIF. In addition, quantitative RT-PCR analysis showed that Gö6983-mediated inhibition of ES cell differentiation on collagen IV was associated with repression of lineage-specific gene expression (FIG. 1D). It was determined whether ES cells maintained their multidifferentiation potential along with the self-renewal ability in presence of Gö6983. It was found that ES cells, maintained for five passages with Gö6983, readily formed EBs or differentiated on collagen IV with induction of lineage-specific gene expression upon withdrawal of Gö6983 (FIG. 1E). These results indicated that active PKC signaling is important for mouse ES cell differentiation and blockade of PKC signaling by a single PKC inhibitor Gö6983 is sufficient to reversibly inhibit differentiation of mouse ES cells under different culture conditions.

EXAMPLE 3

Combinatorial Inhibition of PKC Zeta and Other PKC Isoforms Completely Inhibits ES Cell Differentiation Gö6983 selectively and efficiently inhibits five different PKC isoforms (α, β, γ, δ, and ζ) and at higher concentrations (>20 µM) inhibits isoform PKC µ. As ≧2.5 µM of Gö6983 inhibits mouse ES cell differentiation, it was concluded that PKC µ function may be dispensable for ES cell differentiation under the culture conditions herein. Western blot analysis was performed to determine which of the other five PKC isoforms that are inhibited by Gö6983 are expressed in mouse ES cells at the undifferentiated state and during differentiation. The results of this analysis indicated that all five isoforms were expressed in mouse ES cells. Thus, to determine whether function of a specific PKC isoform or combinatorial functions of multiple PKC isoforms is important for the differentiation potential of ES cells, other pharmacological inhibitors were tested that selectively inhibit specific subsets of PKC isoforms. This analysis indicated that Gö6976 (inhibits PKC α, β2; Martiny-Baron, et al. (1993) *J. Biol. Chem.* 268:9194-9197), Ro-31-8425 (inhibits PKC α, β1, β2, γ and ε; Wilkinson, et al. (1993) *Biochem. J.* 294(Pt. 2):335-337) and Rottlerin (inhibits PKC δ; Gschwendt, et al. (1994) *Biochem. Biophys. Res. Comm.* 199:93-98) could not prevent differentiation of mouse ES cells in absence of LIF. However, Bisindolylmaleimide I was able to inhibit ES cell differentiation, albeit at a lower efficiency than Gö6983. Similar to Gö6983, Bisindolylmaleimide I also inhibits isoform PKC ζ along with PKC α, β1, δ and ε. Thus, it was posited that function of the atypical PKC, PKC ζ, is important for the differentiation potential of mouse ES cells. Western blot analysis of p-PKC ζ showed that indeed PKC ζ phosphorylation in ES cells is almost completely inhibited by Gö6983.

To further demonstrate that Gö6983 treatment impairs PKC ζ function, the phosphorylation of PKC ζ target proteins was analyzed. PKCζ directly phosphorylates the serine 311 (S311) residue of the RelA subunit of the transcription factor NF-κB (Duran, et al. (2003) *EMBO J.* 22:3910-3918). Also, PKCζ directly interacts with and phosphorylates the lethal giant larvae 1 and 2 (LGL1/2) proteins at conserved serine residues (Klezovitch, et al. (2004) *Genes Dev.* 18:559-571; Plant, et al. (2003) *Nature Cell Biol.* 5:301-308). It was observed that Gö6983 treatment impaired the phosphorylation of RelA and LGL1/2 in mESCs, confirming that activity of PKCζ is impaired with Gö6983 treatment.

Figure 2A:
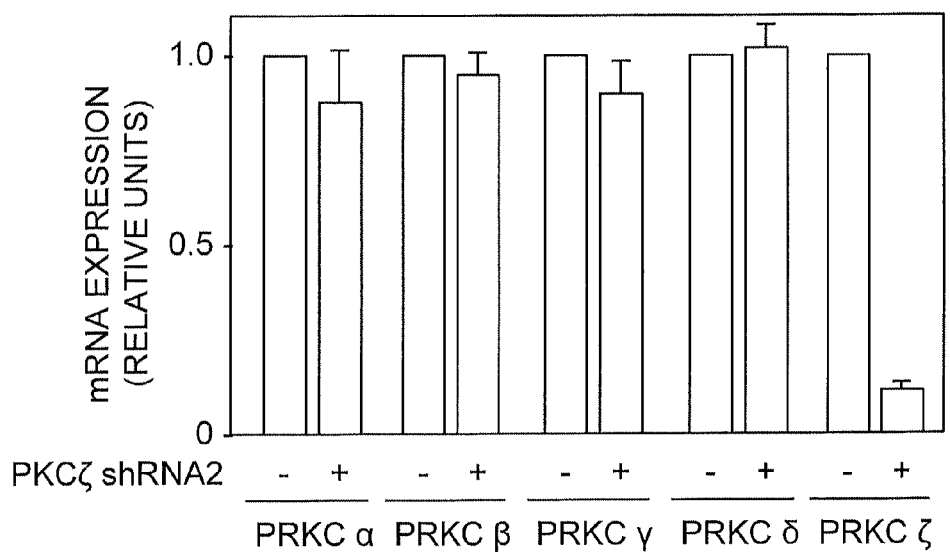
FIG. 2 shows the expression of PKC isoforms (FIG. 2A) upon specific knock-down of PKC ζ and the resulting effect on the expression of pluripotency markers (FIGS. 2B and 2C). Expression of PKC isoforms and pluripotency markers was determined by RT-PCR analysis (mean±standard error). Knock-down cells were grown in the absence of LIF (FIG. 2B) and cultured on collagen IV for 5 days in the presence and absence of Gö6983 (FIG. 2C).
Figure 2B:
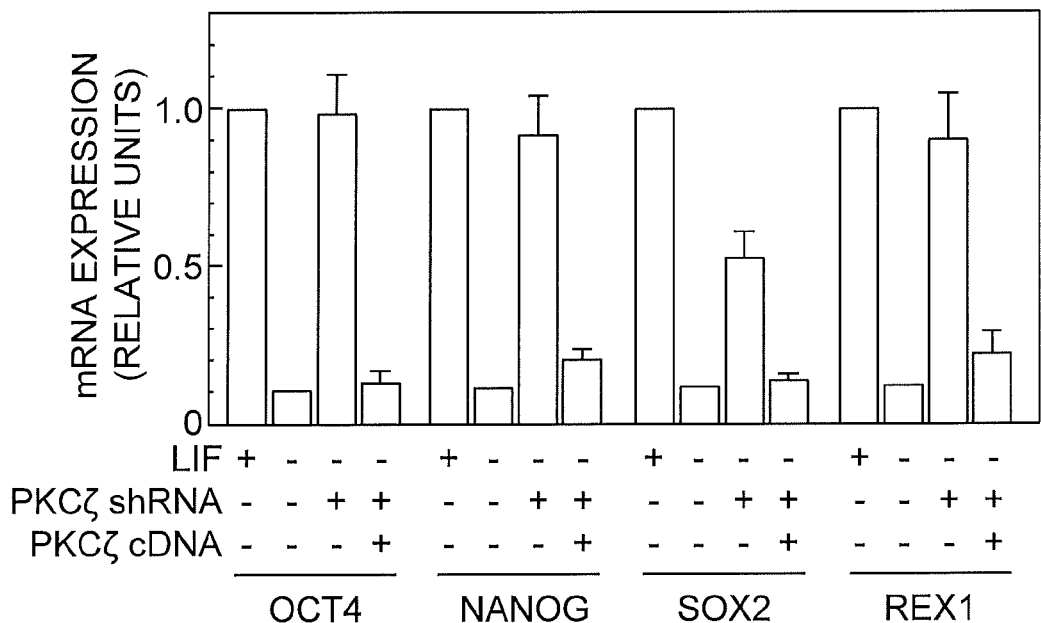

The differentiation potential of mouse ES cells, in which PKC ζ isoform was knocked-down by RNA interference (RNAi), was also determined. For RNAi, a shRNA was designed to specifically target the 3' untranslated region (UTR) of PKCζ and efficiently knock-down its expression in E14 cells. The loss of PKCζ function in PKCζ-knocked-down (PKCζkd) cells was validated based upon the loss of RelAS311 phosphorylation. It was found that, when cultured on gelatin-coated plates for multiple passages and without LIF, the PKCζkd cells maintained undifferentiated ES cell colony morphology and expression of pluripotency markers. Similar results were obtained when PKCζ was specifically knocked-down using a different shRNA construct, which targets the PKCζ coding sequence (FIG. 2A). To demonstrate that impaired mESC differentiation was specifically due to the loss of PKCζ function, an RNAi-immune PKCζ mRNA (without 3'UTR) was ectopically expressed in PKCζkd cells using a lentiviral vector. The viral vector also expressed an enhanced green fluorescence protein (EGFP) cDNA for monitoring ectopic expression of PKCζ. When PKCζ was ectopically expressed from the RNAi-immune construct, the PKCζkd cells readily differentiated in the absence of LIF. To further demonstrate the role of PKCζ in mESC differentiation, PKCζkd cells were cultured at clonal density. It was found that, when cultured at clonal density without LIF, PKCζkd cells maintained undifferentiated colony morphology at a >60% efficiency and also maintained expression of pluripotency markers (FIG. 2B). However, they failed to do so when PKCζ was ectopically expressed from the RNAi immune construct. Moreover, cells ectopically expressing PKCζ had reduced expression of pluripotency markers (FIG. 2B). These results confirm that, without LIF, depletion of PKCζ function maintains undifferentiated cultures of mESCs and implicate an active role of PKCζ in inducing lineage commitment.

Figure 2C:
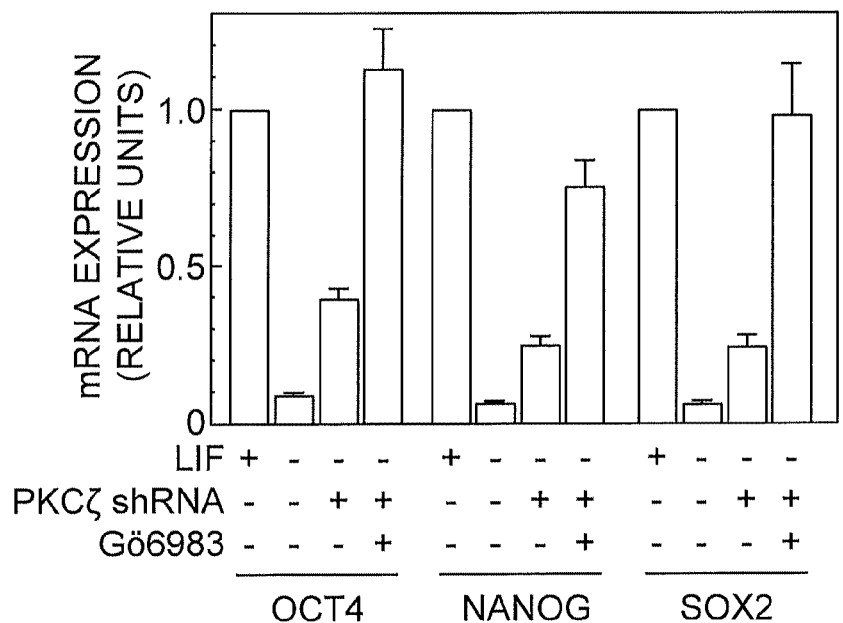

When cultured on collagen IV without LIF, the majority of the PKCζkd cells underwent differentiation along with the presence of some undifferentiated ES cell colonies. However, Gö6983 treatment inhibited differentiation of PKCζkd cells and maintained the expression of pluripotency markers on collagen IV (FIG. 2C). Similar results were also obtained when PKCζkd cells were treated with RA in the presence and absence of Gö6983. Thus, it was concluded that the function of PKCζ alone promotes differentiation in mESCs but a combinatorial function of other PKC isoforms along with PKCζ further potentiate lineage commitment of ES cells.

EXAMPLE 4

Inhibition of PKC Signaling by Gö6983 Maintains the in Vivo Developmental Potential of Mouse ES Cells The developmental potency of mouse ES cells that were maintained for multiple passages in Gö6983 was also examined. E14 ES cells were cultured for 7 passages with Gö6983 and subsequently injected into the blastocyst of C57B1/6 mice to obtain chimeric mice. The blastocyst injection of Gö6983-treated ES cells yielded multiple chimeric mice indicating that culturing mouse ES cells with Gö6983 for multiple passages did not compromise their developmental potency.

Maintenance of self-renewal ability of multiple ES cell-lines in various culture conditions in presence of Gö6983 indicated that inhibition of PKC signaling was sufficient to inhibit ES cell differentiation. However, it did not indicate the involvement of PKC signaling mechanisms in the derivation of ES cell lines from inner cells mass (ICM). To test that, the effects of Gö6983 were investigated on the derivation of ES cells from mouse embryos. Embryonic day 3.5 blastocysts from 129/Sv mice were plated on gelatin-coated plates with Gö6983 and serum, but without LIF and feeder cells. Under these conditions several ES cell colonies were derived from blastocyst outgrowths. Although multiple ES cell colonies were obtained from 10 blastocysts in the presence of serum and Gö6983, 10 ES cell colonies were selected for subsequent analyses. No undifferentiated ES cell colony was obtained from >15 blastocysts without Gö6983, and with serum alone. The newly Gö6983-derived ES cell lines were successfully propagated in an undifferentiated state when cultured at clonal density with Gö6983. After six passages, two different Gö6983-derived ES cell lines were injected into the blastocysts to generate chimera. The Gö6983-derived ES cells successfully generated adult chimera, which produced germline offsprings when crossed with C57BL/6 adults. These results indicate that inhibition of PKC signaling is sufficient to derive germline-competent pluripotent ES cells from mouse blastocyst.

ES cells were readily derived from the 129SV strain when blastocysts were plated directly into Gö6983 on gelatin-coated plates. The established ES cell lines were propagated for multiple passages in Gö6983 and karyotype analysis after 8 passages showed >90% diploid cells. The newly established ES cell lines were propagated on Gö6983, generated adult chimeras, and contributed to the germline.

Multilineage differentiation potential of the established ES cell lines was also determined. This analysis indicated that these cells readily formed embryoid bodies and expressed lineage specific markers when differentiated on collagen IV. These results indicate that pharmacological inhibition of PKC signaling is an efficient way to establish ES cells from mice as well as from other mammalian species.

EXAMPLE 5

PKC Inhibition Maintains Pluripotency Independent of STAT3, PI(3)K-Akt, GSK3, and MAPK-Dependent Pathways Although Gö6983 is a selective PKC inhibitor, along with PKC isoforms, it might inhibit other signaling pathways involved in the maintenance of stem cell pluripotency. Induction of JAK-STAT3 signaling by LIF is a commonly used strategy to maintain undifferentiated mouse ES cell pluripotency. Thus, it was determined whether Gö6983 induces STAT3 phosphorylation in ES cells. Western blot analysis showed that Gö6983 did not induce STAT3 phosphorylation in E14 cells. Furthermore, Gö6983 efficiently prevented differentiation of Stat3$^{-/-}$ (Ying, et al. (2008) supra) ES cells when cultured in serum-free N2B27 medium, indicating that Gö6983-mediated inhibition of ES cell differentiation was independent of JAK-STAT3 signaling pathway. These data are further validated by the observation that Jak-Inhibitor-I, a potent JAK inhibitor (Niwa, et al. (2009) *Nature* 460:118-122), was also ineffective in preventing Gö6983-mediated inhibition of mESC differentiation.

Activation of the PI(3)K-Akt signaling has also been implicated in maintaining mESC pluripotency (Watanabe, et al. (2006) *Oncogene* 25:2697-2707). As PKCζ is a negative regulator of Akt activity in certain contexts (Doornbos, et al. (1999) *J. Biol. Chem.* 274:8589-8596), it was determined whether Gö6983 treatment activates PI(3)K-Akt signaling in mESCs. Similar to an earlier observation (Paling, et al. (2004) *J. Biol. Chem.* 279:48063-48070), it was found that LIF induced Akt phosphorylation in mESCs. However, unlike LIF, Gö6983-mediated inhibition of mESC differentiation was not associated with Akt phosphorylation. Moreover, LY294002, a potent inhibitor of PI3 kinase (Paling, et al. (2004) supra), did not prevent the Gö6983-mediated maintenance of mESC self-renewal. API-59CJ-OMe, a potent Akt inhibitor (Jin, et al. (2004) *Br. J. Cancer* 91:1808-1812), also failed to prevent Gö6983-mediated inhibition of mESC differentiation. However, both LY294002 and API-59CJ-OMe, by themselves, were unable to prevent mESC differentiation in the absence of LIF. These results confirmed that Gö6983-mediated maintenance of ES cell pluripotency was independent of PI3-Akt pathway.

Using small molecule inhibitors, the GSK-3/Wnt/β-catenin pathway has been shown to support an undifferentiated phenotype of both mESCs and human ES cells (Sato, et al. (2004) supra). Furthermore, multiple studies have shown that, in mESCs, GSK-3β phosphorylates c-Myc at threonine 58(T58) residue, which induces degradation of c-Myc Myc and contributes to mESC differentiation (Bechard & Dalton (2009) *Mol. Cell. Biol.* 29:2092-2104). Structurally, Gö6983 is a bis-indolylmaleimide derivative (Gschwendt, et al. (1996) *FEBS Lett.* 392:77-80) and studies have indicated that certain bis-indolylmaleimide derivatives can inhibit GSK-3 activity in mESCs and enhance self-renewal activity in the presence of LIF and serum but not in the absence of LIF (Bone, et al. (2009) *Chem. Biol.* 16:15-27). Therefore, it was determined whether Gö6983 maintains ES cell pluripotency by inhibiting GSK-3 function. Accordingly, it was determined whether Gö6983 treatment alters GSK3 phosphorylation. The results of this analysis indicated that Gö6983 treatment did not significantly change phosphorylation of either GSK-3α or GSK-3β. Next, it was determined whether β-catenin is stabilized by Gö6983 treatment. It was found that Gö6983 did not stabilize β-catenin in mESCs. β-Catenin-mediated transcriptional activation was also determined by analyzing a canonical Wnt reporter (TOPFLASH reporter).

These results indicated that Gö6983 treatment did not induce TOPFLASH reporter activity in mESCs. Moreover, Gö6983 treatment did not inhibit GSK-3β-mediated phosphorylation of c-Myc at T58 residue. Rather, in Gö6983 culture condition, addition of GSK-3 inhibitor, CHIR99021 (Ying, et al. (2008) supra), abolished c-Myc phosphorylation. These data indicate that GSK-3 is fully active in Gö6983-treated ES cells. Therefore, GSK-3 inhibition is not involved in maintenance of pluripotency in the Gö6983-treated mESCs.

It has been demonstrated that inhibition of extracellular signal-regulated kinase 1/2 (ERK1/2) promotes the pluripotency of ES cells (Ying, et al. (2008) supra). Therefore, it was determined whether ERK signaling is functional in Gö6983-treated ES cells. The results of this analysis indicated that Gö6983 did not inhibit ERK1/2 phosphorylation in ES cells. However, a combination of Gö6983 and PD0325901, a potent MEK inhibitor (Ying, et al. (2008) supra), almost completely inhibited ERK1/2 phosphorylation. To further test the functional ERK-signaling in Gö6983-treated cells, phosphorylation of p90Rsk1 (Rsk1), a downstream target of ERK1/2 (Silverman, et al. (2004) Mol. Cell. Biol. 24:10573-10583) was analyzed. ERK1/2 phosphorylates multiple residues of p90Rsk1, including the T359 and S363 residues (Silverman, et al. (2004) supra). It was observed that phosphorylation of Rsk1 was not inhibited by Gö6983 treatment. However, addition of PD0325901 abolished Rsk1 phosphorylation in Gö6983-treated cells. These results indicate that ERK1/2 signaling was fully active in Gö6983-treated mESCs.

Figure 3A:
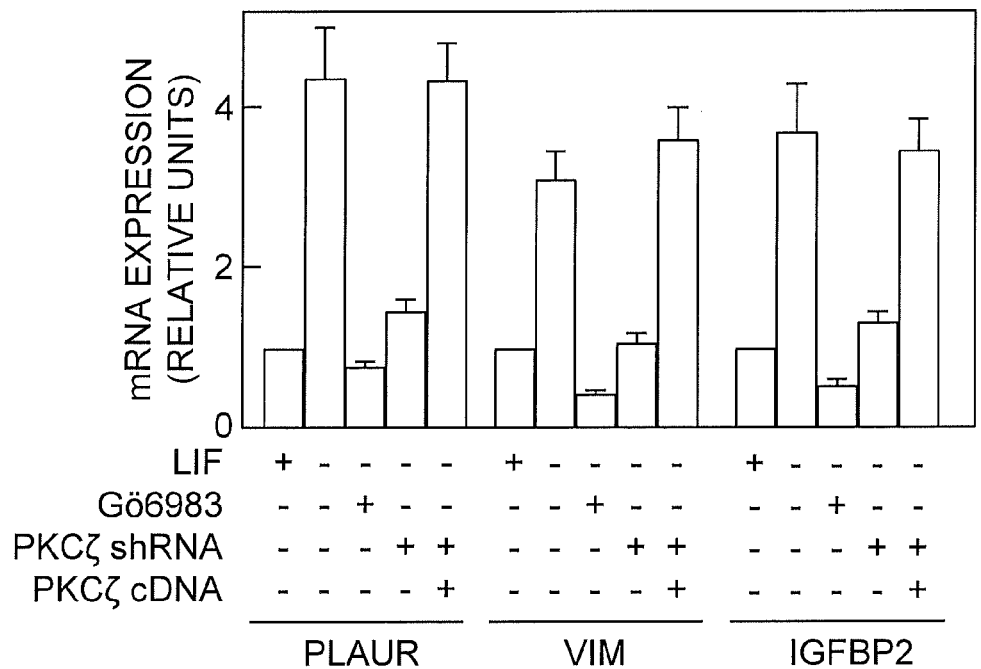
FIG. 3 shows the results of RT-PCR analysis of NF-κB target gene expression in E14 ES cells, cultured with or without LIF and Gö6983, and in PKCζkd cells, with or without ectopic expression of RNAi-immune PKCζ cDNA (FIG. 3A) as well as PKCζkd cells cultured at different culture conditions on collagen IV (FIG. 3B). Data is presented as mean±standard error of three independent experiments. Plaur; plasminogen activator, urokinase receptor, Vim; vimentin, and Igfpb2; insulin-like growth factor binding protein 2.
Figure 3B:
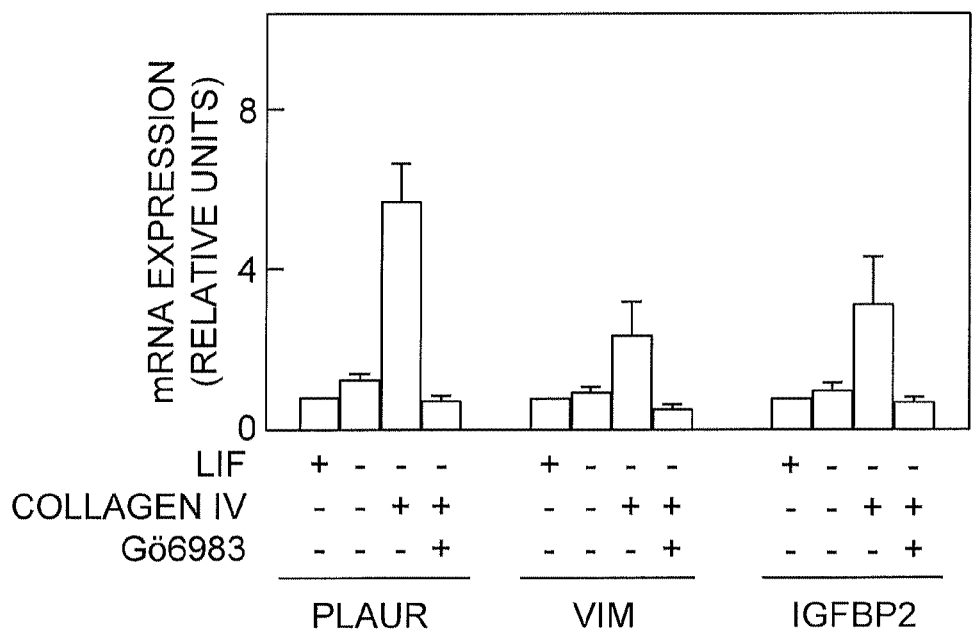

Inhibition of NF-κB activity has been implicated in stem cell pluripotency (Torres & Watt (2008) Nat. Cell Biol. 10:194). PKCζ function is essential for NF-κB transcriptional activity in response to several signaling pathways (Leitges, et al. (2001) Mol. Cell 8:771). Furthermore, it has been shown that, in PKCζ-deficient cells, NF-κB is transcriptionally inactive due to impaired phosphorylation at S311 residue of the RelA subunit (Duran, et al. (2003) supra). Since, both Gö6983 treatment and PKCζ knockdown inhibit RelA phosphorylation at S311 residue in mESCs, and ectopic expression of PKC rescues the phosphorylation in PKCζkd cells, it was determined whether Gö6983-mediated inhibition of mESC differentiation is associated with down-regulation of NF-κB activity. Analysis of mRNA expression showed that, in the absence of LIF, transcription of NF-κB target genes were activated, and Gö6983 treatment inhibited their activation (FIG. 3A). Analysis with PKCζkd cells in the absence of LIF also showed similar results (FIG. 3A). However, ectopic expression of PKCζ rescued activation of NF-κB target genes in PKCζkd cells (FIG. 3A). To further evaluate impairment of NF-κB transcriptional activity, a reporter plasmid was used, in which Luciferase expression is regulated by five NF-κB binding motifs (NFκ5x-Luc reporter). Using this construct, considerable reporter activity was observed in E14 cells in the presence of LIF and the reporter activity was further induced in the absence of LIF. However, reporter gene activation was strongly inhibited upon Gö6983 treatment or in PKCζcd cells. Furthermore, similar to the NF-κB target gene activation, ectopic expression of PKCζ rescued the reporter activity in PKCζkd cells. These data clearly demonstrate that NF-κB is a direct target of PKCζ in ES cells and indicate involvement of a PKCζ-NF-κB signaling axis during lineage commitment in mESCs.

As PKCζkd cells were not able to maintain an undifferentiated phenotype on collagen-IV, it was posited that PKCζ-depletion might not be sufficient to inhibit NF-κB activity in the presence of additional differentiation cues. Therefore, activation of NF-κB target genes, RelA phosphorylation and NFκ5x-Luc reporter activity was analyzed in PKCζcd cells cultured on collagen IV. NF-κB target genes, RelA phosphorylation, as well as the reporter Luciferase, were significantly activated in PKCζkd cells cultured on collagen IV and Gö6983 treatment inhibited the activation. Thus, in the presence of additional differentiation cues, other mechanisms can induce NF-κB activity in PKCζkd cells. The strong inhibition of NF-κB activity in Gö6983-treated PKCζkd cells might be mediated by Nanog, which directly inhibits NF-κB activity (Torres & Watt (2008) supra). This is supported by the observation that Gö6983 treatment maintained expression of Nanog in PKCζkd cells on collagen IV.

EXAMPLE 6

Inhibition of PKC Signaling by Gö6983 Maintains the ES Cell-Specific Chromatin Marks As epigenetic mechanisms dictate ES cell self-renewal vs. differentiation, it was contemplated that inhibition of PKC function contributes to the maintenance of ES-cell-specific chromatin structure, thereby preventing induction of developmental genes and differentiation. One of the epigenetic components, repressive trimethylation on lysine 27 of histone H3 (H3K27me3) by PRC2 at developmental genes has been implicated in stem cell pluripotency (Boyer, et al. (2006) Nature 441:349; Pasini, et al. (2007) Mol. Cell Biol. 27:3769). It was determined whether Gö6983 treatment maintains PRC2-mediated H3K27 methylation at developmental regulator genes. In mESCs, Gö6983 treatment maintained high levels of H3K27me3 and chromatin occupancy of enhancer of zeste 2 (EZH2), the catalytic histone methyl transferase subunit (Cao, et al. (2002) Science 298:1039-1043) of the PRC2 complex, at the developmental regulator genes. Ezh2$^{-/-}$ ES cells were used to further assess PRC2 association in Gö6983-mediated maintenance of pluripotency. It was found that, in the absence of LIF, differentiation could be efficiently induced in Ezh2$^{-/-}$ cells cultured on collagen-IV. However, Gö6983 treatment completely inhibited collagen-IV-induced Ezh2$^{-/-}$ cell differentiation, and maintained expression of pluripotency markers without the induction of developmental regulator genes.

It has been shown that EZH2 homolog EZH1 compensates for loss of EZH2 in Ezh2–/– ES cells (Shen, et al. (2008) Mol. Cell 32:491). Therefore, ES cells lacking EED (embryonic ectoderm development, Eed–/– cells), the common core subunit for EZH1 and EZH2 containing complexes, were analyzed. Like Ezh2–/– cells, Eed–/– cells could not maintain undifferentiated colony morphology when cultured on collagen IV without LIF. But, they largely maintained undifferentiated colony morphology and expression of pluripotency markers with Gö6983. However, expression of developmental regulator genes was significantly induced even in the presence of Gö6983. Predictably, ChIP analyses showed that induction of mRNA expression of developmental regulator genes in Eed–/– cells was associated with loss of H3K27Me3 modification and Suz12 recruitment at their chromatin domains. Increased expression of developmental genes observed in Gö6983-treated Eed–/– ES cells indicated that the maintenance of mESC pluripotency by Gö6983 was associated with characteristic repressive H3K27 methylation at developmental regulator genes and PRC2 function was important to suppress their expression.

Subsequently, it was determined how Gö6983 treatment maintained expression of pluripotency genes. Accordingly, epigenetic mechanisms that are implicated in the regulation of Oct4 and Nanog expression were analyzed. During ES cell differentiation, silencing of the Oct4 and Nanog genes is associated with de novo DNA methylation at their regulatory regions (Epsztejn-Litman, et al. (2008) *Nat. Struct. Mol. Biol.* 15:1176-1183; Li, et al. (2007) *Mol. Cell. Biol.* 27:8748-8759). It was determined whether Gö6983 treatment prevented DNA methylation at the regulatory regions of these genes by bisulfite sequencing and methylation specific PCR (MSP). For this analysis, E14 cells were cultured for 5 days on collagen-IV with or without LIF and Gö6983. It was found that in the presence of both LIF and Gö6983, the promoter regions of Oct4 and Nanog remained largely unmethylated. Studies have indicated that, during mESC differentiation, tri-methylation at lysine 9 residue of histone H3 (H3K9Me3) by the histone methyltransferase G9A precedes the DNA methylation at the Oct4 locus (Epsztejn-Litman, et al. (2008) supra). H3K9 methylation is also implicated in silencing Nanog expression during mESC differentiation (Loh, et al. (2007) *Genes Dev.* 21:2545-2557). Thus, it was tested whether Gö6983 treament prevented H3K9 methylation at the Oct4 and Nanog loci. It was found that similar to LIF, Gö6983 treatment inhibited H3K9 methylation at those loci. On the other hand, in Gö6983-treated cells. both Oct4 and Nanog loci contained high levels of H3K4 methylation (H3K4Me3), a mark for transcriptionally active genes. Collectively, in Gö6983-treated cells, the presence of characteristic epigenetic marks at the pluripotency genes along with the presence of repressive H3K27me3 modification at the developmental regulator genes indicated that Gö6983 treatment did not bypass the requirement of a proper ES cell-specific epigenetic state.

EXAMPLE 7

Inhibition of PKC Facilitates Derivation of iPSCs

Figure 4A:
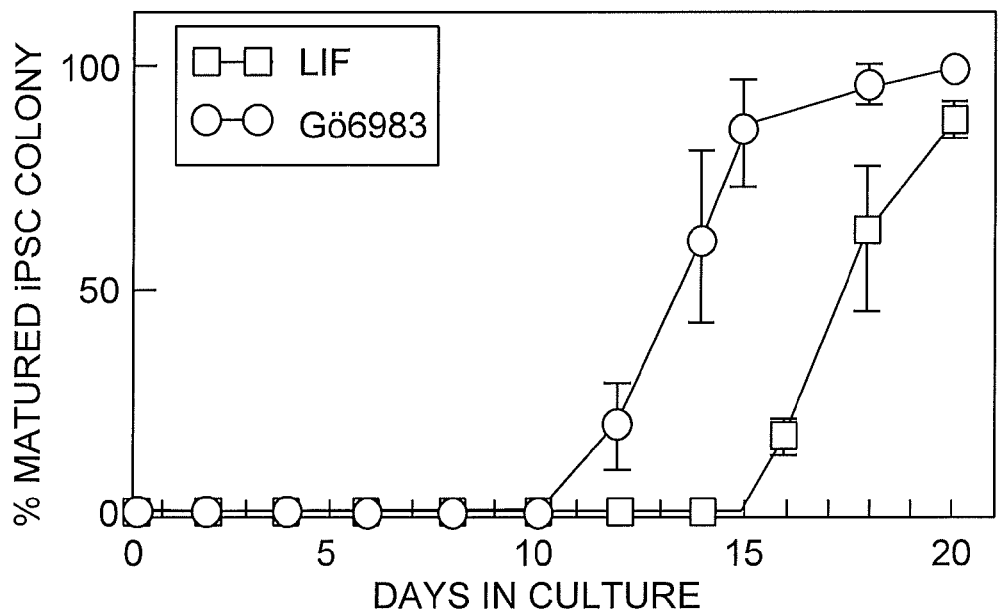
FIG. 4 shows the time course of iPSC colony formation (FIG. 4A) and relative number of iPSC colonies that were derived in the presence of LIF and Gö6983 (FIG. 4B).
Figure 4B:
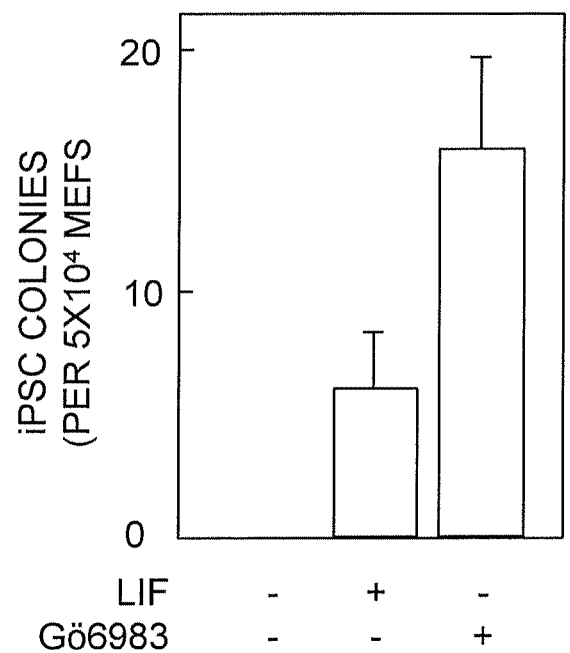

Induced pluripotent stem cells, commonly abbreviated as iPS cells or iPSCs, are a type of pluripotent stem cell artificially derived from a non-pluripotent cell, typically an adult somatic cell, by inducing "forced" expression of certain genes (Takahashi & Yamanaka (2006) supra). Therefore, it was determined whether Gö6983 could facilitate derivation of iPSCs. 129Sv MEFs were infected with lentiviral vectors encoding the four reprogramming factors Oct4, Sox2, KLF4 and cMyc, and cultured in the presence or absence of Gö6983 or LIF. Several ES cell-like iPSC colonies appeared 12 days after culturing with Gö6983. Those iPSCs were readily propagated at clonal density with Gö6983 and expression of pluripotency markers was confirmed. Moreover, Gö6983-derived iPS cells were injected into blastocysts and shown to generate chimeric mice. Compared to LIF, iPSC colonies (defined by the expression of Nanog and Rex-1) were obtained at a significantly faster rate in the presence of Gö6983 (FIG. 4A). Furthermore, at the culture conditions herein, the efficiency of obtaining matured iPSC colonies was three fold higher with Gö6983 compared to LIF (FIG. 4B). These results indicate that inhibition of PKC isoform by Gö6983 provides an efficient culture condition for reprogramming of differentiated cells to iPSCs.

EXAMPLE 8

Inhibition of PKC Maintains Human ES Cells in an Undifferentiated State

Figure 5:
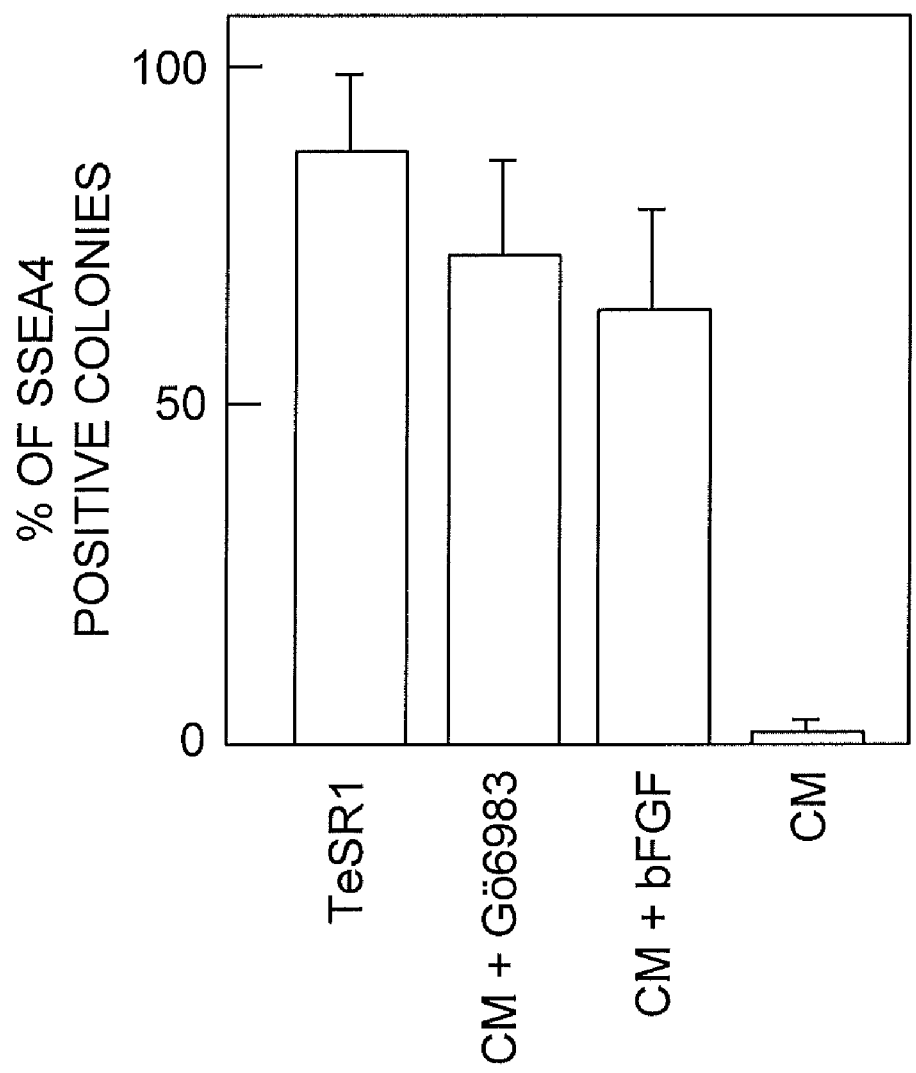
FIG. 5 shows that human ES cells treated with Gö6983 exhibited levels of SSEA4 expression comparable to cultures grown in TeSR1 medium or conditioned medium containing bFGF, which maintain human ES cell pluripotency.

To demonstrate that PKC inhibition is useful in maintaining the undifferentiated state of human ES cells were grown in the presence of Gö6983 in feeder-free cultures. It was observed that human ES cells (H9 cells), cultured in MEF-conditioned medium with Gö6983 maintained their undifferentiated morphology and expression of pluripotency marker, stage-specific embryonic antigen 4 (SSEA4) (Adewumi, et al. (2007) *Nat. Biotechnol.* 25:803), after multiple passages of incubation. Notably, similar to cultures in TeSR1 medium (Ludwig, et al. (2006) *Nat. Methods* 3:637) or conditioned medium with bFGF (Amit, et al. (2000) *Dev. Biol.* 227:271) that maintain human ES cells pluripotency, sustained high levels of SSEA4 expression was observed in the majority of Gö6983-treated H9 colonies (FIG. 5). High levels of Oct4 protein expression was also observed in the Gö6983-treated human ES cells in contrast to a substantial reduction of Oct4 expression in differentiated cells cultured with conditioned medium alone.

In addition to ES and iPS cells, it was determined whether blockade of PKC signaling facilitated the propagation of cancer stem cells. To that end, mamosphere formation of a breast cancer cell type known as DCIS.com was analyzed. Mamospheres are specialized structures formed by breast cancer cell types and are indicative of presence and propagation of breast cancer stem cells. It was observed that blockade of PKC signaling by Gö6983 efficiently generated mamospheres from DCIS.com cells. Therefore, blockade of PKC signaling can be used to efficiently propagate and expand cancer stem cells.

These results indicate that PKC signaling is important to dictate maintenance of stem-ness vs. differentiation of stem or progenitors cells in multiple contexts. Therefore, targeting PKC signaling pathway can be useful for expansion of tissue-specific stem cell populations, like hematopoietic stem cells and the like, and also to generate tissue-specific differentiated cell types from progenitor cells.

What is claimed is:
1. A PKC inhibitor having the structure:
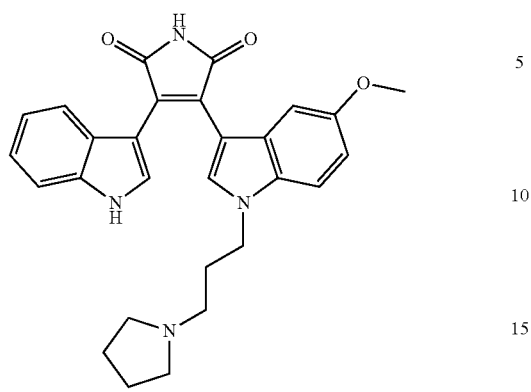
or a pharmaceutically acceptable salt or, hydrate thereof.
* * * * *